United States Patent
Arugula et al.

(10) Patent No.: US 11,127,966 B2
(45) Date of Patent: Sep. 21, 2021

(54) HEMATIN MODIFIED BILIRUBIN OXIDASE CATHODE

(71) Applicant: CFD Research Corporation, Huntsville, AL (US)

(72) Inventors: Mary Arugula, Huntsville, AL (US); Erica Wagner Pinchon, Huntsville, AL (US); Sameer Singhal, Huntsville, AL (US); Yevgenia Ulyanova, Huntsville, AL (US)

(73) Assignee: CFD Research Corporation, Huntsville, AL (US)

(*) Notice: Subject to any disclaimer, the term of this patent is extended or adjusted under 35 U.S.C. 154(b) by 149 days.

(21) Appl. No.: 16/266,950

(22) Filed: Feb. 4, 2019

(65) Prior Publication Data

US 2020/0028181 A1 Jan. 23, 2020

Related U.S. Application Data

(60) Provisional application No. 62/626,529, filed on Feb. 5, 2018, provisional application No. 62/626,531, filed on Feb. 5, 2018.

(51) Int. Cl.
*H01M 4/90* (2006.01)
*C12N 11/14* (2006.01)
(Continued)

(52) U.S. Cl.
CPC .......... *H01M 8/16* (2013.01); *C12N 9/0004* (2013.01); *C12N 11/14* (2013.01); *H01M 4/622* (2013.01);
(Continued)

(58) Field of Classification Search
CPC ........ H01M 8/16; H01M 4/9008; H01M 4/90; C12N 11/14
See application file for complete search history.

(56) References Cited

U.S. PATENT DOCUMENTS

2005/0041458 A1* 2/2005 Lossau ............... G11C 13/0019
365/151
2006/0269826 A1* 11/2006 Katz ....................... H01M 4/90
429/401
(Continued)

OTHER PUBLICATIONS

L. Xin, Z. Zhang, Z. Wang and L. Wenzhen, "Simultaneous Generation of Mesoxalic Acid and Electricity from Glycerol on a Gold Anode Catalyst in Anion-Exchange Membrane Fuel Cells," ChemCatChem, vol. 4, pp. 1105-1114, 2012.
(Continued)

*Primary Examiner* — Imran Akram
(74) *Attorney, Agent, or Firm* — Mascoff Brennan; Jonathan M. Benns

(57) ABSTRACT

A cathode can include: an electrode substrate; a porphyrin precursor attached to the substrate; and an enzyme coupled to the electrode substrate to be associated with the porphyrin precursor, the enzyme reduces oxygen. The cathode can include a conductive material associated with the porphyrin precursor and/or the enzyme. The cathode can include 1-pyrenebutanoic acid, succinimidyl ester (PBSE) associated with the porphyrin precursor and/or the enzyme and/or the conductive material. The cathode can include 2,5-dimethyl-1-phenyl-1H-pyrrole-3-carbaldehyde (DMY-Carb) associated with the 1-pyrenebutanoic acid, succinimidyl ester (PBSE) and/or the porphyrin precursor and/or the enzyme and/or the conductive material. The porphyrin precursor is attached to the substrate through covalent coupling. In some aspects, substrate is linked to the porphyrin precursor, the porphyrin precursor is linked to the conductive material, the conductive material is linked to the PBSE, the PBSE is linked to the DMY-carb, and the DMY-carb is linked to the enzyme.

25 Claims, 16 Drawing Sheets

(51) Int. Cl.
- H01M 8/16 (2006.01)
- C12N 9/02 (2006.01)
- H01M 4/66 (2006.01)
- H01M 8/1007 (2016.01)
- H01M 4/96 (2006.01)
- H01M 4/92 (2006.01)
- H01M 4/62 (2006.01)
- B82Y 30/00 (2011.01)

(52) U.S. Cl.
CPC ............ *H01M 4/663* (2013.01); *H01M 4/90* (2013.01); *H01M 4/9008* (2013.01); *H01M 4/92* (2013.01); *H01M 4/96* (2013.01); *H01M 8/1007* (2016.02); *B82Y 30/00* (2013.01); *C12Y 101/01001* (2013.01); *C12Y 101/01002* (2013.01); *C12Y 101/99035* (2013.01); *C12Y 102/02001* (2013.01); *C12Y 102/03004* (2013.01); *C12Y 103/03005* (2013.01)

(56) References Cited

U.S. PATENT DOCUMENTS

| | | | |
|---|---|---|---|
| 2008/0248354 A1* | 10/2008 | Kubo | H01M 8/16 429/458 |
| 2010/0004521 A1* | 1/2010 | Epps | A61B 5/411 600/347 |
| 2010/0209968 A1* | 8/2010 | Akers | C12N 11/08 435/68.1 |
| 2010/0314248 A1* | 12/2010 | Worden | C12Q 1/005 204/403.14 |
| 2011/0250510 A1* | 10/2011 | Cinquin | C12N 9/0006 429/401 |
| 2013/0095351 A1* | 4/2013 | Gellett | H01G 9/035 429/9 |
| 2014/0065494 A1* | 3/2014 | Fujita | H01M 4/9083 429/401 |
| 2015/0364784 A1* | 12/2015 | Babanova | H01M 8/16 429/401 |
| 2016/0006039 A1* | 1/2016 | Cosnier | H01G 11/86 429/7 |
| 2017/0299581 A1* | 10/2017 | Worden | G01N 33/948 |
| 2017/0335363 A1* | 11/2017 | Takahashi | C12Q 1/002 |
| 2018/0138538 A1* | 5/2018 | Ramasamy | C12N 9/0095 |
| 2019/0064100 A1* | 2/2019 | Sode | G01N 27/3272 |

OTHER PUBLICATIONS

G. L. Brett, Q. He, C. M. P. J. Hammond, N. Dimitratos, M. Sankar, A. A. Herzing, M. Conte, J. A. Lopez-Sanchez, C. J. Kiely, D. W. Knight, S. H. Taylor and G. and Hutchings, "Selective Oxidation of Glycerol by Highly Active Bimetallic Catalysts at Ambient Temperature under Base-Free Conditions," Communications, vol. 50, pp. 10136-10139, 2011.

A. Villa, S. Campisi, K. M. H. Mohammed, N. Dimitratos, F. Vindigni, M. Manzoli, W. Jones, M. Bowker, G. J. Hutchings and L. Prati, "Tailoring the selectivity of glycerol oxidation by tuning the acid-base properties of Au catalyst," Catalysis Science and Technology, vol. 5, pp. 1126-1132, 2015.

E. Pinchon, M. Arugula, K. Pant, and S. Singhal, "Enhancement of Electrochemical Performance of Bilirubin Oxidase Modified Gas Diffusion Biocathode by Porphyrin Precursor," Advances in Physical Chemistry, vol. 2018, 9 pages, 2018. doi.org/10.1155/2018/4712547.

M. Arugula, E. Pinchon, K. Pant, S.D. Minteer, S. Singhal, "Enhancement of Electrochemical performance of Bilirubin Oxidase Modified Gas Diffusion Biocathode by Porphyrin Precursor," In: Proceedings from the Electrochemical Society Meetings; May 13-17, 2018; Seattle, WA. Abstract MA2018-01 2245.

M. Arugula, E. Pinchon, U. Lindstrom, P. Juzang, K. Pant, S.D. Minteer, S. Singhal, "Hybrid Non-Enzymatic and Enzymatic Cascade Bioanode for Glycerol/O2 Biofuel Cell Applications," In: Proceedings from the Electrochemical Society Meetings; May 13-17, 2018; Seattle, WA. Abstract MA2018-01 2251.

* cited by examiner

HEMATIN MODIFIED BILIRUBIN OXIDASE CATHODE

CROSS-REFERENCE

This patent application claims priority to U.S. Provisional No. 62/626,529 filed Feb. 5, 2018 and to U.S. Provisional No. 62/626,531 filed Feb. 5, 2018, which are both incorporated herein by specific reference in their entirety.

GOVERNMENT RIGHTS

This invention was made with government support under W911NF-16-C-0081 awarded by the Army Research Office. The government has certain rights in the invention.

BACKGROUND

Previously, conductive inks have been described in connection with electrodes and power generation. Conductive inks can be on electrodes of bio-batteries, which use a biological substance in the power generation. Examples include enzymatic biofuel cell technologies.

Enzymatic biofuel cell technology has demonstrated the possibility of producing electrical power from chemical energy using biological catalysts for powering portable and implanted electronic devices. However, this technology has been limited by insufficient power and shell life compared to existing commercial, non-biological fuel cells. During the last 20 years, significant advancements have been made in improving the overall performance of the biofuel cells with incorporation of hybrid nanostructures including carbon and metal-based nanomaterials and combinations thereof with enzymes. Typically, biofuel cell cathodes utilize a single enzyme system, while a cascade of reactions for deeper and more complete oxidation of fuel is frequently necessary at the anodes.

However, it would be advantageous to continue developing enzymatic biofuel cell technologies.

SUMMARY

In one embodiment, a cathode can include: an electrode substrate; a porphyrin precursor attached to the substrate; and an enzyme coupled to the electrode substrate so as to be associated with the porphyrin precursor, wherein the enzyme reduces oxygen. In some aspects, the cathode can include a conductive material associated with the porphyrin precursor and/or the enzyme. In some examples, the conductive material is selected from the group consisting of carbon black powder, carbon black (Vulcan XCc-72, E-tek), carbon black, carbon powder (Formula BT™, Superior Graphite), carbon fiber single wall carbon nanotubes (SWCNT), multi-wall carbon nanotubes (MWCNT), double walled nanotubes, carbon nanotubes arrays, diamond-coated conductors, glassy carbon and mesoporous carbon. Carbon based materials are graphite, uncompressed graphite worms, delaminated purified flake graphite (Superior graphite), high performance graphite, highly ordered pyrolytic graphite, pyrolytic graphite and polycrystalline graphite, and combinations thereof. In some aspects, the cathode includes 1-pyrenebutanoic acid, succinimidyl ester (PBSE) being associated with the porphyrin precursor and/or the enzyme and/or the conductive material. In some aspects, the cathode includes 2,5-dimethyl-1-phenyl-1H-pyrrole-3-carbaldehyde (DMY-Carb) being associated with the 1-pyrenebutanoic acid, succinimidyl ester (PBSE) and/or the porphyrin precursor and/or the enzyme and/or the conductive material. In some aspects, the porphyrin precursor is attached to the substrate through covalent coupling. In some aspects, the porphyrin precursor is attached to the substrate through covalent coupling with 1-ethyl-3-(3-dimethylaminopropyl) carbodiimide hydrochloride (EDC), and N-hydroxysuccinimide (NHS). In some aspects, the enzyme, conductive material, PBSE, and DMY-carb are combined together by mixing and applied to the porphyrin precursor. In some aspects, the porphyrin precursor links a mixture of the enzyme, conductive material, PBSE, and DMY-carb to the substrate. In some aspects, substrate is linked to the porphyrin precursor, the porphyrin precursor is linked to the conductive material, the conductive material is linked to the PBSE, the PBSE is linked to the DMY-carb, and the DMY-carb is linked to the enzyme. In some aspects, the substrate is linked to the porphyrin precursor, the porphyrin precursor is linked to the conductive material, and the conductive material is linked to the enzyme via a linker. In some aspects, the PBSE and DMY-carb are the linkers. In some aspects, the linker can include N-hydroxybenzotriazole or N-hydroxysuccinimide. 1-ethyl-3-(3-dimethylaminopropyl) carbodiimide, N,N'-dicyclohexyl carbodiimide, N,N'-diisopropyl carbodiimide, bis(trimethylsilyl)carbodiimide and N-cyclohexyl-N'-(β-[N-methylmorpholino]ethyl)carbodiimide p-toluenesulfonate, Dithiobis(succinimidyl)propionate (DSP) or 4,4'-[8,16-Dihydro-9,16-dioxodibenzo[a,j] perylene-2,10-diyl)dioxy]dibutyric acid di(N-succinimidyl ester) (DDPSE) (Dithiobis(succinimidyl)propionate), or combination thereof or combinations with other recited linkers.

In some embodiments, the porphyrin precursor is hematin. In some aspects, the porphyrin precursor is an electron transfer moiety.

In some embodiments, the cathode is devoid of a mediator.

In some embodiments, the enzyme is bilirubin oxidase (BOx). In some aspects, the enzyme is bilirubin oxidase (BOx), and/or the conductive material is multi-wall carbon nanotubes (MWCNT).

In some embodiments, the cathode includes a binder associated with the porphyrin precursor and enzyme. In some aspects, the cathode includes a binder associated with the porphyrin precursor, enzyme, conductive material, PBSE, and DMY-Carb. In some aspects, the cathode includes a binder being selected from the group consisting of tetramethyl orthosilicate (TMOS), tetraethyl orthosilicate (TEOS), and combinations thereof.

In some embodiments, the porphyrin precursor is present at a concentration from about 5 mM to about 10 mM; the enzyme is present at a concentration from about 11 Units/mL to about 15 Units/mL; the conductive material is present at a concentration from about 1% to about 2%; the PBSE is present at a concentration from about 5 to about 7 mM; and the DMY-Carb is present at a concentration from about 5 mM to about 7 mM. In some aspects, the porphyrin precursor is present at an amount from about 36 to about 80 mg/mL; the enzyme is present at an amount from about 1 mg/cm$^2$ to about 14 mg/cm$^2$; the conductive material is present at an amount from about 5 mg to about 15 mg; the PBSE is present at an amount from about 2 mg to about 5 mg; and the DMY-Carb is present at an amount from about 1 mg to about 5 mg.

In some embodiments, the electrode substrate is selected from the group consisting of carbon felt, buckypaper, pressed teflonized carbon black powder, pressed teflonized carbon black powder having carbon nanotubes, buckeye composite, carbon felt, buckeye paper, toray paper, glassy carbon, carbon cloth, carbon paper (toray), carbon paper (ELAT), carbon screen printed electrodes, and combinations thereof.

In some embodiments, the cathode can include an alkaline substance associated with the porphyrin precursor and/or enzyme. In some aspects, the cathode can include an alkaline substance between the substrate and the porphyrin precursor and/or enzyme. In some aspects, a hydroxide is the alkaline substance. In some aspects, KOH or NaOH is an alkaline substance on the substrate or associated with the porphyrin precursor and/or enzyme.

In some embodiments, a cathode region of a biofuel cell can include the cathode of one of the embodiments and a neutral fuel liquid in contact with the cathode, the neutral fuel liquid having a neutral pH. In some aspects, the neutral fuel liquid includes the fuel reagent. In some aspects, the fuel reagent is an alcohol, polyol, carbohydrate, or combination thereof. In some aspects, the neutral fuel liquid includes an aqueous buffer. In some aspects, the fuel reagent is ethylene glycol or glycerol. In some aspects, an anode is configured to convert the fuel reagent to carbon dioxide.

In some embodiments, a fuel cell can include: the cathode of one of the embodiments; an anode; and a neutral fuel liquid in contact with the anode and cathode, wherein the neutral fuel liquid has a neutral pH and the fuel reagent.

In some embodiments, the anode includes an anode enzyme. In other embodiments, the anode is devoid of an anode enzyme.

In some embodiments, the fuel cell is a biofuel cell. In some aspects, the anode is a bio-anode. In other embodiments, the anode is not a bio-anode.

In some embodiments, the anode is a hybrid anode with a region devoid of an anode enzyme and a region having an anode enzyme. In some aspects, the fuel cell is devoid of a mediator. In some aspects, the anode is devoid of a membrane. In some aspects, the anode is devoid of a membrane as a separator.

In some embodiments, a manufacturing method of making a cathode can include: forming an electrode substrate; attaching a porphyrin precursor to the electrode substrate; and linking an enzyme to the substrate so as to be associated with the porphyrin precursor, wherein the enzyme reduces oxygen. In some aspects, the method can include: forming the electrode substrate by: combining teflonized carbon black powder and carbon nanotubes; and pressing the teflonized carbon black powder and carbon nanotubes into the electrode substrate. In some embodiments, the porphyrin precursor is with a hydroxide.

In some embodiments, the manufacturing method can include: treating the electrode substrate with EDC and NETS; combining the porphyrin precursor with a hydroxide; and depositing the porphyrin precursor and hydroxide on the treated electrode substrate. In some aspects, the method can include combining EDC and NHS with the porphyrin precursor and a hydroxide to form a solution, and depositing the solution on the treated electrode substrate.

In some embodiments, the manufacturing method can include preparing a BOx ink as follows: forming an alcoholic aqueous solution; adding carbon nanotubes to the alcoholic aqueous solution; adding DMY-carb to a solvent; combining the DMY-carb in solvent with the alcoholic aqueous solution having the carbon nanotubes; and adding PBSE to the composition having the DMY-carb and carbon nanotubes.

In some embodiments, the manufacturing method can include depositing a BOx ink on the electrode substrate having the porphyrin precursor. In some aspects, the method includes depositing a binder on the substrate having the porphyrin precursor and BOx ink. In some aspects, the method includes depositing tetramethyl orthosilicate (TMOS) on the substrate having the porphyrin precursor and BOx ink. In some aspects, the method includes depositing tetramethyl orthosilicate (TMOS) by chemical vapor deposition on the substrate having the porphyrin precursor and BOx ink.

In some embodiments, a method of producing electrical power can include: providing the fuel cell of one of the embodiments; and operating the fuel cell to produce electrical power with the neutral fuel liquid having the neutral pH and the fuel reagent.

In some embodiments, there is potentiostat for electrochemical measurements.

In some embodiments, a fuel cell can include: the cathode of one of the embodiments; an anode comprising: an anode electrode substrate; a first region of the anode substrate having a gold nanoparticle composition located thereon; and a second region of the anode substrate having an enzyme composition located thereon. In some aspects, the first region and second region are separate regions; and a neutral fuel liquid in contact with the anode and cathode, the neutral fuel liquid having a neutral pH and the fuel reagent. In some aspects, the gold nanoparticle composition includes a conductive material mixed with the gold nanoparticles. In some aspects, the gold nanoparticle composition includes a binder mixed with the gold nanoparticles. In some aspects, the gold nanoparticle composition includes a binder mixed with the gold nanoparticles and conductive material.

In some embodiments, the binder is a polymer. In some examples, the binder polymer is selected from the group consisting of polytetrafluoroethylene (PTFE), polytetrafluoroethylene (PTFE, such as Dupont Teflon®) and polyvinylidene fluoride (PVDF, such as Arkema Kynar®, Nafion, Polyhexafluoropropylene and fluorinated ethylene-propylene copolymers (FEP), vinylidene fluoride-trifluorochloroethylene copolymer (PVDF-PCTFE), Nonfluorinated binders including polyethylene, polypropylene, ethylene-propylene copolymer or ethylene-propylene-diene (EPDM) rubbers (such as ExxonMobil), Nonfluorinated binders including polyethylene, polypropylene, ethylene-propylene copolymer or ethylene-propylene-diene (EPDM) rubbers (such as ExxonMobil), and combinations thereof.

In some embodiments, the anode electrode substrate is selected from the group consisting of carbon felt, buckyeyepaper, carbon cloth, carbon paper (toray), carbon paper (ELAT), carbon screen printed electrodes, and combinations thereof.

In some embodiments, the gold nanoparticle composition includes platinum mixed with the gold nanoparticles. In some aspects, the gold nanoparticle composition includes platinum mixed with the gold nanoparticles and/or conductive material and/or binder. In some aspects, the anode substrate has a surface and the gold nanoparticle composition is deposited on a first portion of the surface and the enzyme composition is deposited on a second portion of the surface. In some aspects, the gold nanoparticle composition includes magnesium oxide (MgO). In some aspects, the gold nanoparticle composition includes platinum, carbon black powder, and/or MgO.

In some embodiments, the enzyme composition includes an enzyme selected from the group consisting of oxalate decarboxylase (OxDc), oxalate oxidase (OxO), aldehyde dehydrogenase (ALDH), alcohol dehydrogenase (ADH), formate dehydrogenase, formaldehyde dehydrogenase, glucose dehydrogenase, lactic dehydrogenase and pyruvate dehydrogenase, and combinations thereof.

In some embodiments, an alkaline substance is associated with the gold nanoparticle composition. In some aspects, an alkaline substance is electrodeposited onto the electrode substrate. In some aspects, a hydroxide is the alkaline substance. In some aspects, KOH or NaOH is an alkaline substance on the anode substrate.

In some embodiments, about half of a surface of the anode substrate includes the gold nanoparticle composition and about half of the surface of the anode substrate includes the enzyme composition. In some aspects, more than about half of a surface of the anode substrate includes the gold nanoparticle composition and less than about half of the surface of the anode substrate includes the enzyme composition. In some aspects, a portion of the gold nanoparticle composition overlaps with a portion of the enzyme composition.

In some embodiments, the enzyme composition includes carbon nanotubes as a conductive material. In some aspects, the enzyme composition includes ethylene glycol diglycidyl ether (EGDE). In some aspects, the enzyme composition includes EGDE and conductive material. In some aspects, the enzyme composition includes 10% EGDE and CFDRC ink (SWCNT-PEI) having aqueous solution of single wall carbon nanotube (SWCNT) conductive agent, PEI binding agent, and NHS/EDC as cross-linkers.

In some embodiments, the anode can include a hydroxide between the gold nanoparticle composition and anode substrate.

In some embodiments, the anode can include: a first anode substrate having a first gold nanoparticle composition region and a first enzyme composition region; and a second anode substrate having a second gold nanoparticle composition region and a second enzyme composition region. In some aspects, the first anode substrate contacts the second anode substrate such that the first gold nanoparticle composition contacts the second gold nanoparticle composition and the first enzyme composition contacts the second enzyme composition.

In some embodiments, the anode can include: an anode substrate having a hydroxide composition thereon; a first region of the anode substrate having a gold nanoparticle composition located thereon on the hydroxide composition; and a second region of the anode substrate having an enzyme composition located thereon on the hydroxide composition, wherein the combination of the gold nanoparticle composition and enzyme composition converts a fuel reagent to carbon dioxide at neutral pH. In some aspects, the first region and second region are separate regions.

In addition to the illustrative aspects, embodiments, and features described above, further aspects, embodiments, and features will become apparent by reference to the drawings and the following detailed description.

BRIEF DESCRIPTION OF THE FIGURES

The foregoing and following information as well as other features of this disclosure will become more fully apparent from the following description and appended claims, taken in conjunction with the accompanying drawings. Understanding that these drawings depict only several embodiments in accordance with the disclosure and are, therefore, not to be considered limiting of its scope, the disclosure will be described with additional specificity and detail through use of the accompanying drawings.

Figure 1:
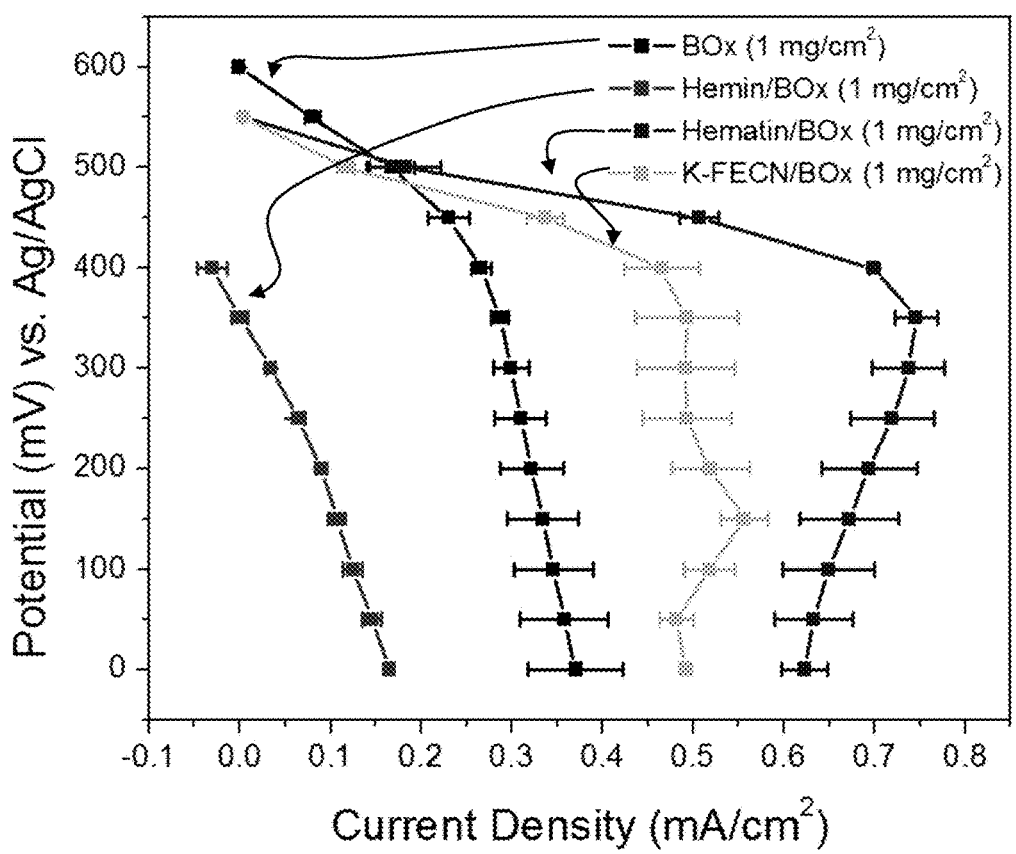
FIG. 1 shows data for representative polarization curves for air breathing cathodes modified with BOx only, hemin/BOx, hematin/BOx, or K-FECN/BOx.

The elements and components in the figures can be arranged in accordance with at least one of the embodiments described herein, and which arrangement may be modified in accordance with the disclosure provided herein by one of ordinary skill in the art.

DETAILED DESCRIPTION

In the following detailed description, reference is made to the accompanying drawings, which form a part hereof. In the drawings, similar symbols typically identify similar components, unless context dictates otherwise. The illustrative embodiments described in the detailed description, drawings, and claims are not meant to be limiting. Other embodiments may be utilized, and other changes may be made, without departing from the spirit or scope of the subject matter presented herein. It will be readily understood that the aspects of the present disclosure, as generally described herein, and illustrated in the figures, can be arranged, substituted, combined, separated, and designed in a wide variety of different configurations, all of which are explicitly contemplated herein.

Generally, the present technology relates to enzymatic biofuel cells that can use any alcohol (e.g., methanol, ethanol, etc.) or sugar (e.g., glucose, sucrose, etc.) or polyol (e.g., glycerol, ethylene glycol, antifreeze etc.) for an alcohol based biofuel cell. The biofuel cells can include an assembly of a hybrid enzymatic anode and a bilirubin oxidase (BOx) biocathode. The hybrid anode can be configured to utilize non-enzymatic oxidation of glycerol by inorganic nanoparticles, and enzymatic nanocomposites can be used for conversion of a final byproduct in order to achieve efficient energy production from glycerol.

In one embodiment, the biofuel cell can be constructed to be devoid of a mediator. Also, the biofuel cell can be constructed to be devoid of a membrane. Accordingly, the biofuel cell without the mediator or the membrane has been utilized to achieve a maximum open circuit voltage (OCV) greater than 600 mV, power output of 0.7 mW/cm$^2$, and maximum current density of 3.0 mA/cm$^2$ with 0.1 M glycerol at neutral pH. The fuel cell demonstrated significant discharge capacity of 600 mAh/g under 0.25 mA constant current load. The enzymatic/non-enzymatic hybrid strategy can be further extended to develop other polyol (e.g. ethylene glycol and antifreeze) based biofuel cells.

Polyol based fuel cells can provide high currents in the presence of an alkali electrolyte such as 1M KOH or 2M KOH (pH 14). However, the high pH is not feasible for biofuel cell systems with use of enzymes to catalyze alcohols (e.g., polyols) such as glycerol and ethylene glycol, and is a problem for the enzymes at the cathode side that reduce oxygen. Accordingly, a hybrid anode having gold nanoparticles (AuNPs) can now be used in biofuel cell systems due to the ability to catalyze glycerol and/or ethylene glycol using phosphate buffer solution (PBS) buffer at pH 7. This allows the anode to be used with an enzymatic cathode, such as a BOx cathode.

Embodiments of the anode may include the first region having the gold nanoparticle composition. The gold nanoparticles may be combined with a conductive material (e.g., nano-scale conductive material) with or without a binder mixed with the gold nanoparticles and/or the conductive material. The anodes described herein can be used with multicopper oxidase (MCO) enzymes-based biocathodes to enhance oxygen reduction. Also, the anodes described herein can be used with biocathodes modified with natural substrates specific for MCO enzymes, which may provide improvement for oxygen reduction. For example, the anodes may be used with 1-pyrenebutanoic acid, succinimidyl ester (PBSE) and 2,5-dimethyl-1-phenyl-1H-pyrrole-3-carbaldehyde (DMY-Carb) oriented bilirubin oxidase (BOx) modified gas diffusion biocathodes. Now, it has been found that such BOx biocathodes can be improved by incorporating a porphyrin precursor (e.g., hematin) as an electron transfer moiety. The porphyrin precursor (e.g., hematin) modified BOx cathodes can provide a direct electron transfer reaction of BOx that has a larger O2 reduction current density in phosphate buffer solution (pH 7.0). Also, the porphyrin precursor modified BOx cathodes can be used without a mediator. These porphyrin precursor modified BOx cathodes can provide catalytic currents with a 2.5 fold increase compared to non-modified oriented BOx electrodes. Moreover, these porphyrin precursor modified BOx cathodes can provide a mediator-less and compartment-less Glucose/O2 biofuel cell based on direct electron transfer (DET) type bioelectrocatalysis via the BOx-cathode and the glucose dehydrogenase (GDH)-anode. These porphyrin precursor modified BOx cathodes can provide peak power densities of 1 mW/cm$^2$ at pH 7.0 with 100 mM glucose/10 mM NAD fuel. The maximum current density of 1.6 mA/cm$^2$ and the maximum power density of 0.4 mW/cm$^2$ were achieved at 300 mV with a non-modified BOx cathode, while the significantly higher 3.5 mA/cm$^2$ and 1.1 mW/cm$^2$ of current and power density was achieved with the porphyrin precursor modified BOx cathode. The performance improved 2.4 times due to the porphyrin precursor acting as a natural substrate and activator for BOx activity enhancement.

The fuel for the biofuel cell can include alcohols and carbohydrates. An example can include polyols, such as glycerol and ethylene glycol.

The anode for the biofuel cell can include a conductive ink deposited on at least a portion of an anode substrate. The conductive ink can include standard components.

The conductive ink may be used without a mediator (electron transfer mediator). In one example, the biofuel cell can be devoid of hydroquinone.

In the embodiments of the electrically conductive ink described herein that is used on the anode, the electrically conductive ink exhibits increased retention of electrical conductivity and biocatalytic activity at increased temperatures when compared to prior art electrically conductive inks. For example, the electrically conductive ink retains significant electrical conductivity and biocatalytic activity at temperatures above 40 degrees Celsius or above 50 degrees Celsius as compared to prior art ink. In a particular embodiment, the electrically conductive inks of the present disclosure retain 75%, 80%, 85%, 90%, 95%, or greater of their electrical conductivity and biocatalytic activity while operating or being stored at increased temperatures (such as over 40 and 55 degrees Celsius) as compared to 22 degrees Celsius.

The embodiments of the electrically conductive ink include a nano-scale conducting material. The nano-scale conducting material may serve several functions including, but not limited to, providing a large surface area to volume for charge transfer ratios that increase the electrode's total biocatalytic reaction rates, immobilizing and stabilizing the enzyme (when the enzyme is included), and facilitating efficient electron transfer from the enzyme directly to the anode. In one embodiment, the nano-scale conducting material is a carbon nanotube (CNT). CNTs are cylinder (or tube) shaped molecules of graphitic carbon that have remarkable electronic properties and many other unique characteristics. In yet a further embodiment of the present disclosure, the CNT may either be a single walled or a multi-walled CNT. Single walled CNTs comprise a single rolled layer of graphite carbon while multi-walled CNTs comprise multiple rolled layers (or concentric tubes) of graphite. In yet a further embodiment, the single- or multi-walled CNT may be functionalized. Functionalized CNTs have additional chemical molecules or functional groups attached to their sidewalls and display increased solubility in aqueous liquids and polymer resins as compared to non-functionalized CNTs. In one further embodiment, the CNT has been functionalized by the addition of a carboxylic acid (COOH) group; however, functionalization with other groups including without limitation: hydroxyl (OH), amines ($NH_2$), bromine (Br), and others, including larger biomolecules, are possible and should be considered within the scope of this invention. Additionally, carbon black powder may be used as the nano-scale conducting material.

In the embodiments of the electrically conductive ink, the electrically conductive ink incorporates a binding agent. The binding agent is miscible or soluble in aqueous solutions. The binding agent serves to immobilize the nano-scale conductive material, the one or more enzymes and other components of the ink. The binding agent may be any suitable agent as selected by one skilled in the art and may include polymers and other suitable compounds. In one embodiment, the water miscible binding agent is polymer. In one embodiment, the polymer is a cationic polymer, such as, but not limited to, polyethyleneimine (PEI) polymer. Another example of the binder can be polytetrafluoroethylene (PTFE).

Embodiments of the anode may include the second region having the enzyme composition. In one example, the enzyme composition can include oxalate decarboxylase (OxDc).

Additionally, the cathode may also include an enzyme. In certain embodiments, more than one enzyme may be present on the cathode and/or anode. In one embodiment the enzyme may be a single oxidoreductase enzyme capable of oxidizing or reducing a substrate to release or consume electrons which may then be used to create an electric potential/current. As is known to those skilled in the art, oxidoreductase enzymes may be oxidases, dehydrogenases or hydrogenases. In one embodiment, the oxidoreductase enzyme is an oxidase which is capable of oxidizing a carbohydrate substrate. By way of non-limiting example, in one particular embodiment, the oxidase enzyme may be glucose oxidase. In yet a further embodiment, the oxidoreductase enzyme may be dehydrogenase, such as pyrrolo-quinoline-quinone (PQQ) glucose dehydrogenase, D-fructose-5-dehydrogenase, glucose dehydrogenase, alcohol dehydrogenase, gluconate 2-dehydrogenase, laccase, bilirubin oxidase, ascorbate oxidase, aldehyde dehydrogenase, oxalate oxidase, malate dehydrogenase, succinate dehydrogenase, pyruvate dehydrogenase, glutamate dehydrogenase, isocitrate dehydrogenase, or lactase dehydrogenase. As will be realized by one skilled in the art, the choice of one or more enzymes may be influenced by the substrate upon which the one or more enzymes act, the availability of the substrate and other concerns such as the desired operating environment of the electrically conductive ink.

Preferred enzymes for the anode include oxalate decarboxylase (OxDc), oxalate oxidase (OxO), aldehyde dehydrogenase (ALDH), alcohol dehydrogenase (ADH), alcohol oxidase (AOx), or oxalate deformalyase (OxDf).

Preferred enzymes for the cathode include bilirubin oxidase (BOx), laccase (Lac), ascorbate oxidase (AOx), cytochrome oxidase (Cyt Ox), multicopper oxidases (MCOs).

In one embodiment of the present disclosure, the substrate may be a simple or complex carbohydrate, such as, but not limited to, glucose, fructose, sucrose, trehalose, glycerol, or an alcohol, such as, but not limited to, methanol or ethanol, or a polyol such as glycerol or ethylene glycol or others, such as diethylene glycol, polyethylene glycol, diol, and commercial antifreeze such as Prestone and others.

Cathode Experimental

A series of hemin, hematin, and K-FECN (e.g., potassium, iron, cyanide) modified air breathing cathodes were prepared including BOx. After the enhancing agents were completely dry on the electrode surface, standard lead selenide 2,5-dioxopyrrolidin-1-yl 4-(pyren-1-yl)butanoate (PBSE, also known as 1-pyrenebutanoic acid, succinimidyl ester)/$N^1$-((ethylimino)methylene)-$N^3$,$N^3$-dimethylpropane-1,3-diamine (DMY-carb)/bilirubin oxidase (BOx) (PBSE/DmyCarb/BOx) (1 mg/cm$^2$) multi-wall carbon nanotube (MWCNT) ink was deposited onto the cathodes followed by tetramethyl orthosilicate (TMOS) vapor deposition. The BOx cathodes were allowed to dry at 4° C. overnight prior to electrochemical testing. FIG. 1 displays current density polarization curves for BOx, hemin/BOx, hematin/BOx, and K-FECN/BOx air breathing cathodes. The highest current densities were achieved for the hematin/BOx cathodes followed by the K-FECN/BOx cathodes. FIG. 1 shows data for representative polarization curves for air breathing cathodes modified with BOx only, hemin/BOx, hematin/BOx, or K-FECN/BOx.

Figure 2:
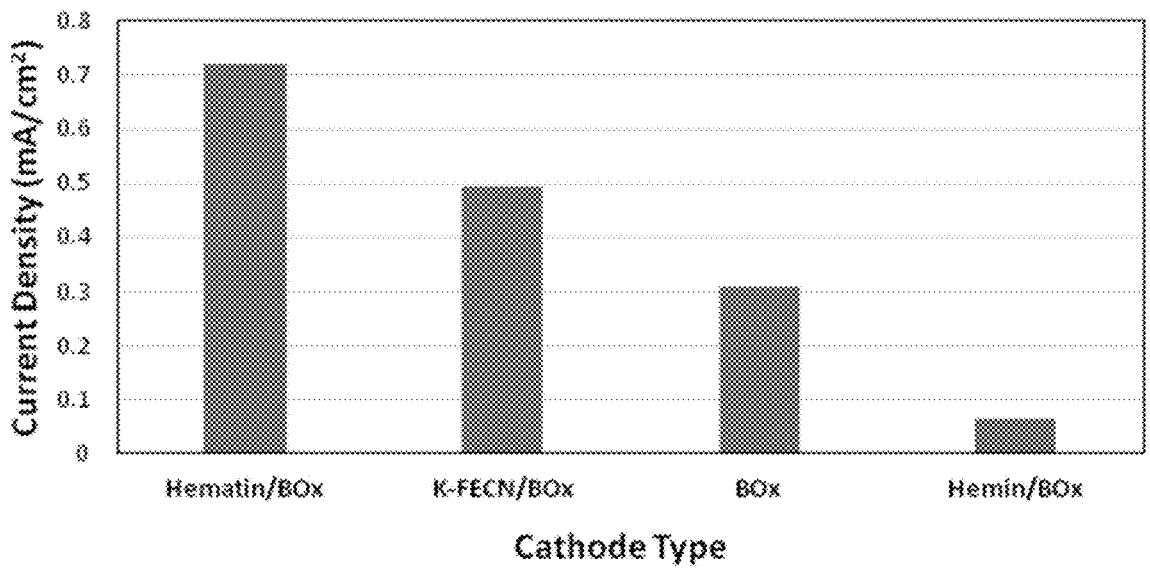
FIG. 2 provides data for the current density output at 250 mV for hematin/BOx, K-FECN/BOx, BOx, and hemin/BOx air breathing cathodes tested in a standard PBS buffer.

FIG. 2 compares the performance of the hematin/BOx, K-FECN/BOx, BOx, and hemin/BOx air breathing cathodes at 250 mV. The hematin/BOx air breathing cathodes performed over 2 times better than the standard BOx cathodes. The hemin/BOx air breathing cathodes performed poorly. Although hemin and BOx can both serve as catalysts for the oxygen reduction reaction (ORR), hemin appears to inhibit BOx activity, which would explain why the BOx air breathing cathodes outperformed the hemin/BOx cathodes. FIG. 2 provides data for the current density output at 250 mV for hematin/BOx, K-FECN/BOx, BOx, and hemin/BOx air breathing cathodes tested in standard PBS buffer.

Figure 3:
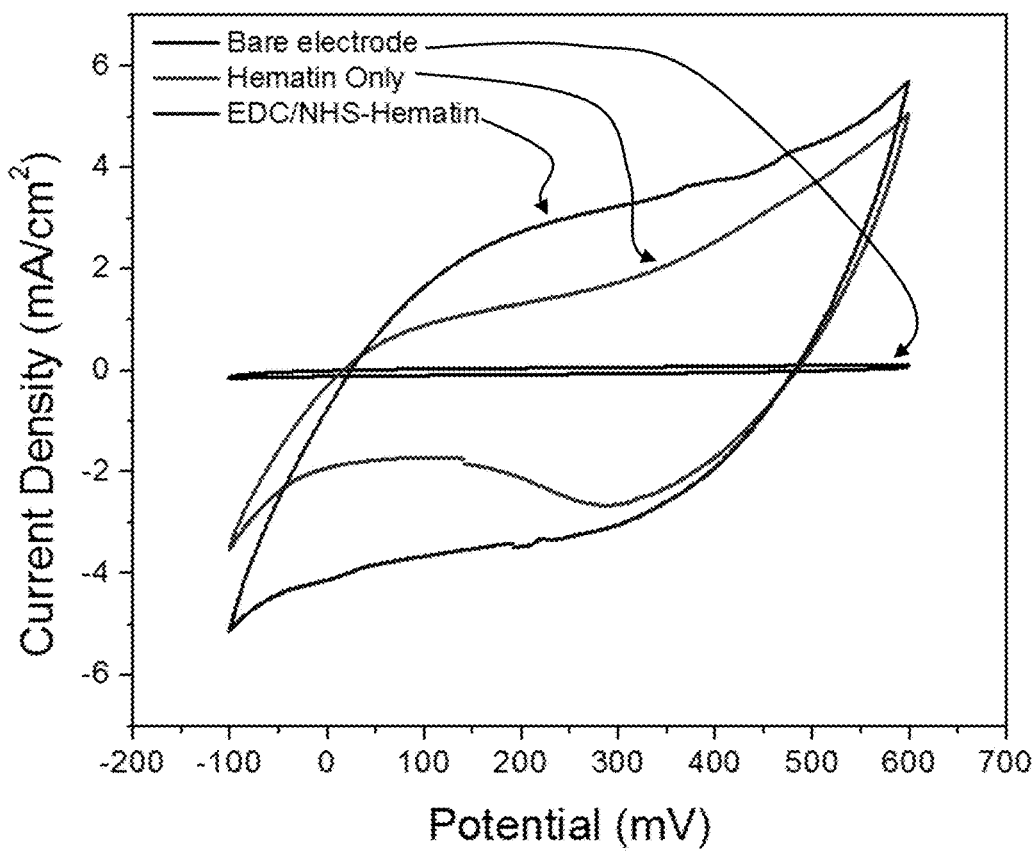
FIG. 3 shows data of representative CV curves for a bare, hematin, and EDC/NHS-hematin modified air breathing cathodes tested in a 245 mM PBS buffer.

A cyclic voltammetry (CV) study was conducted to compare the electrochemical behavior of hematin-modified air breathing cathodes to air breathing cathodes modified with EDC/NHS-hematin (e.g., EDC is 1-ethyl-3-(3-dimethylaminopropyl)carbodiimide hydrochloride, and NHS is N-hydroxysuccinimide). The following settings were used for the CV testing: a potential range of 600 to −100 mV, a total of 20 cycles, and a scan rate of 250 mV/s. FIG. 3 displays the results of the CV study. As expected, a bare air breathing cathode results in very little current. The hematin-modified air breathing cathodes had a peak reduction peak at around 300 mV. The current density at the peak was 3 mA/cm$^2$. No clear oxidation peaks were observed. Since no reversible redox reaction was observed for the hematin-modified air breathing cathodes, hematin most likely does not serve as a mediator for BOx. Hematin most likely acts as a precursor for oxygen reduction reaction (ORR) at the BOx cathode via an unknown mechanism. The reduction peak for the hematin-modified electrodes disappears once hematin was paired with the EDC/NHS crosslinking couple. FIG. 3 shows data of representative CV curves for a bare electrode, hematin, and EDC/NHS-hematin modified air breathing cathodes tested in 245 mM PBS buffer.

Figure 4:
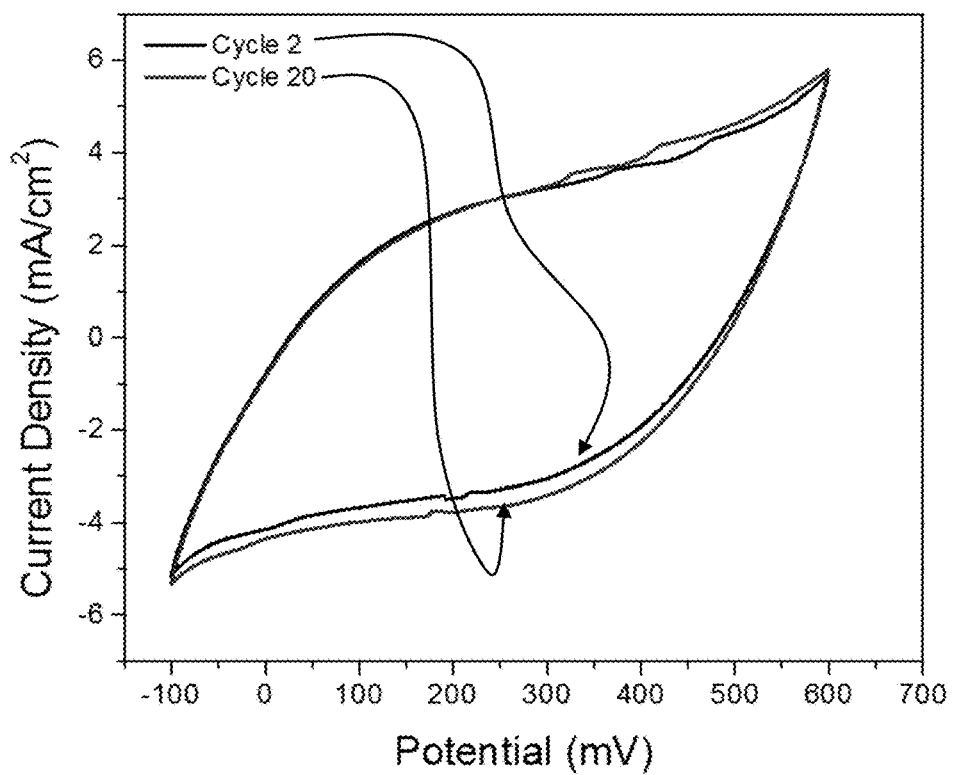
FIG. 4 shows data of representative CV curves comparing cycle 2 and cycle 20 of EDC/NHS-hematin modified air breathing cathodes tested in 245 mM PBS buffer.

A high scan rate of 250 mV/s was employed for the CV study to test the stability of the EDC/NHS-hematin air breathing cathodes. FIG. 4 compares cycle 2 to cycle 20 for the air breathing cathodes modified with EDC/NHS-hematin. There was little variation between the magnitude of cycle 2 and 20. Shrinking CV curves would suggest that the EDC/NHS-hematin was being stripped from the electrode surface. The results of this study suggest that the air breathing cathodes modified with EDC/NHS-hematin were stable. FIG. 4 shows data of representative CV curves comparing cycle 2 and cycle 20 of EDC/NHS-hematin modified air breathing cathodes tested in 245 mM PBS buffer.

Figure 5:
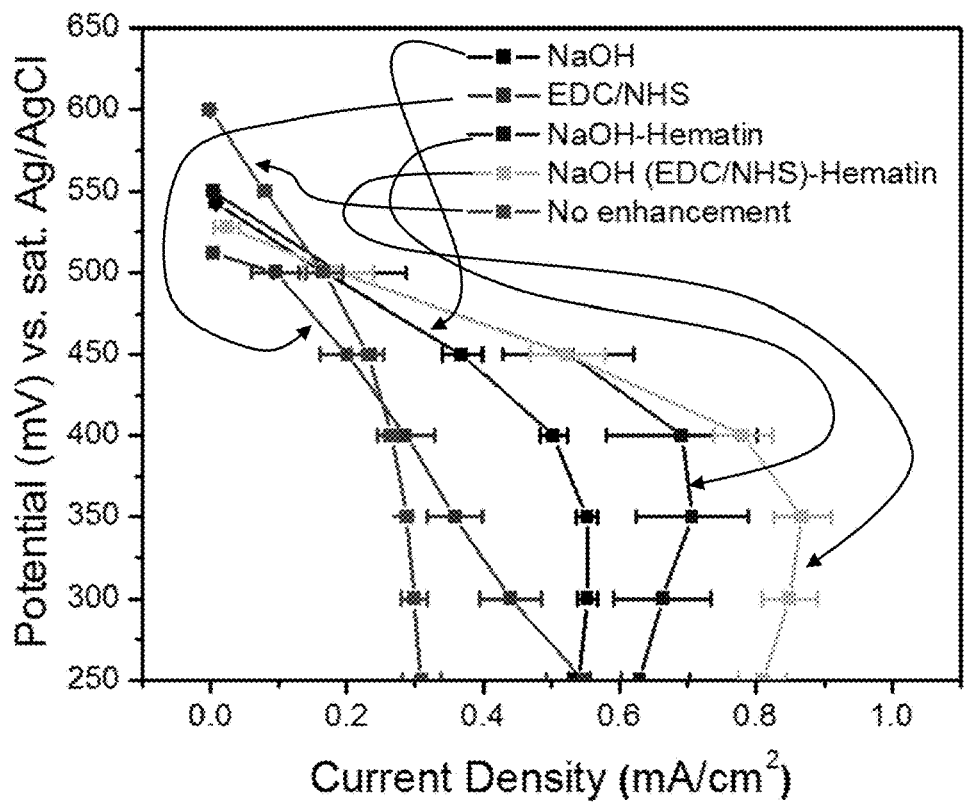
FIG. 5 shows data for representative step potential curves for NaOH, EDC/NHS, NaOH-hematin, NaOH (EDC/NHS)-hematin, and non-enhanced BOx air breathing cathodes tested in 245 mM PBS buffer.

In addition to CV stability studies, step potential studies were conducted. Step potential curves for BOx cathodes modified with NaOH, NaOH-hematin, and NaOH (EDC/NHS)-hematin have been compared. An additional step potential curve was generated, a 2 cm$^2$ air breathing cathode was modified with EDC/NHS (water). BOx ink was then immobilized on top of the EDC/NHS layer following previously described procedures. All BOx cathode types were tested in triplicate. The results for this study are displayed in FIG. 5. The EDC/NHS BOx air breathing cathodes performed better than the BOx only cathodes at 300 mV, but performed significantly less than the NaOH, NaOH-hematin, and NaOH (EDC/NHS)-hematin BOx cathodes. The NaOH (EDC/NHS)-hematin BOx cathodes remained the highest performing cathodes. FIG. 5 shows data for representative step potential curves for NaOH, EDC/NHS, NaOH-hematin, NaOH (EDC/NHS)-hematin, and non-enhanced BOx air breathing cathodes tested in 245 mM PBS buffer.

Figure 6:
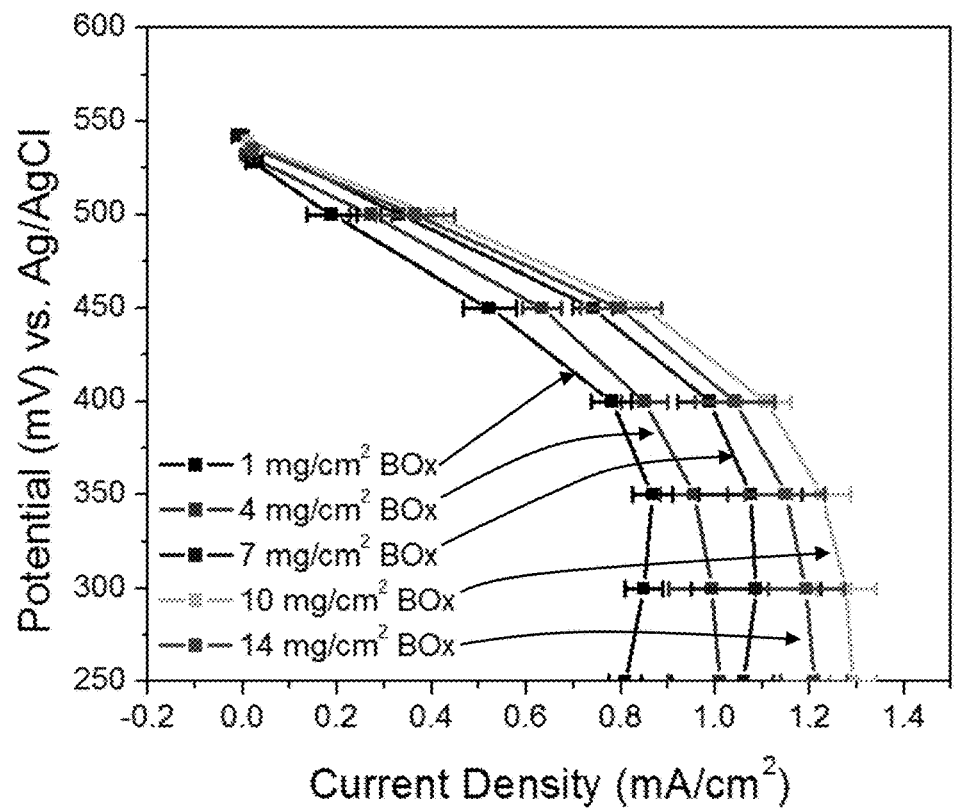
FIG. 6 shows data for representative step potential curves for hematin modified air breathing cathodes with various BOx concentrations.

BOx loading optimization on the hematin-modified air breathing cathodes was conducted. All previous testing was conducted with 1 mg/cm$^2$ BOx loading. Several different BOx concentrations were tested on the air breathing cathodes: 1 mg/cm$^2$, 4 mg/cm$^2$, 7 mg/cm$^2$, 10 mg/cm$^2$, and 14 mg/cm$^2$, and thereby the BOx can be present at any of these amounts or in any range between any of these amounts. FIG. 6 displays representative step potential curves for hematin-modified air breathing cathodes with various concentrations of BOx. The 10 mg/cm$^2$ BOx cathodes displayed the highest electrochemical performance. The average current density for the 10 mg/cm$^2$ BOx cathodes exceeded 1.2 mA/cm$^2$ at 300 mV. FIG. 6 shows data for representative step potential curves for hematin modified air breathing cathodes with various BOx concentrations.

Figure 7:
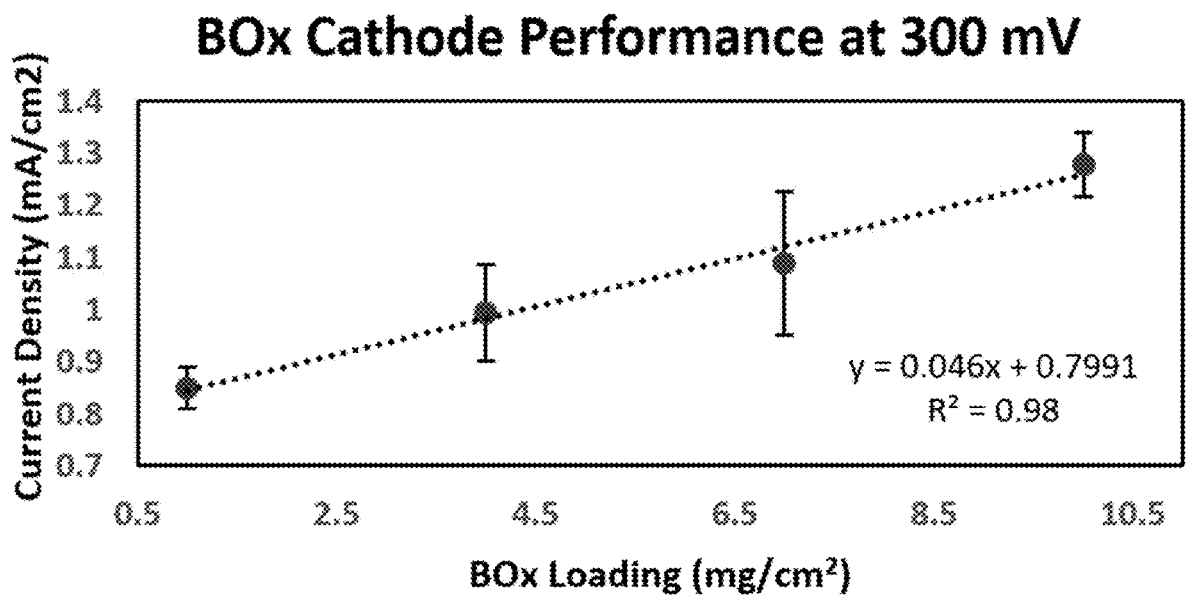
FIG. 7 shows a linear regression line demonstrating the relationship between current density and BOx loading.

A linear increase in performance at 300 mV was seen when the concentration of BOx loading ranged from 1 mg/cm$^2$ to 10 mg/cm$^2$ (FIG. 7). Previously, the optimal BOx loading was 14 mg/cm$^2$. By modifying the cathode with hematin prior to BOx immobilization, the optimal loading for BOx was reduced by 28.6%. FIG. 7 shows a linear regression line demonstrating the relationship between current density and BOx loading.

Figure 8:
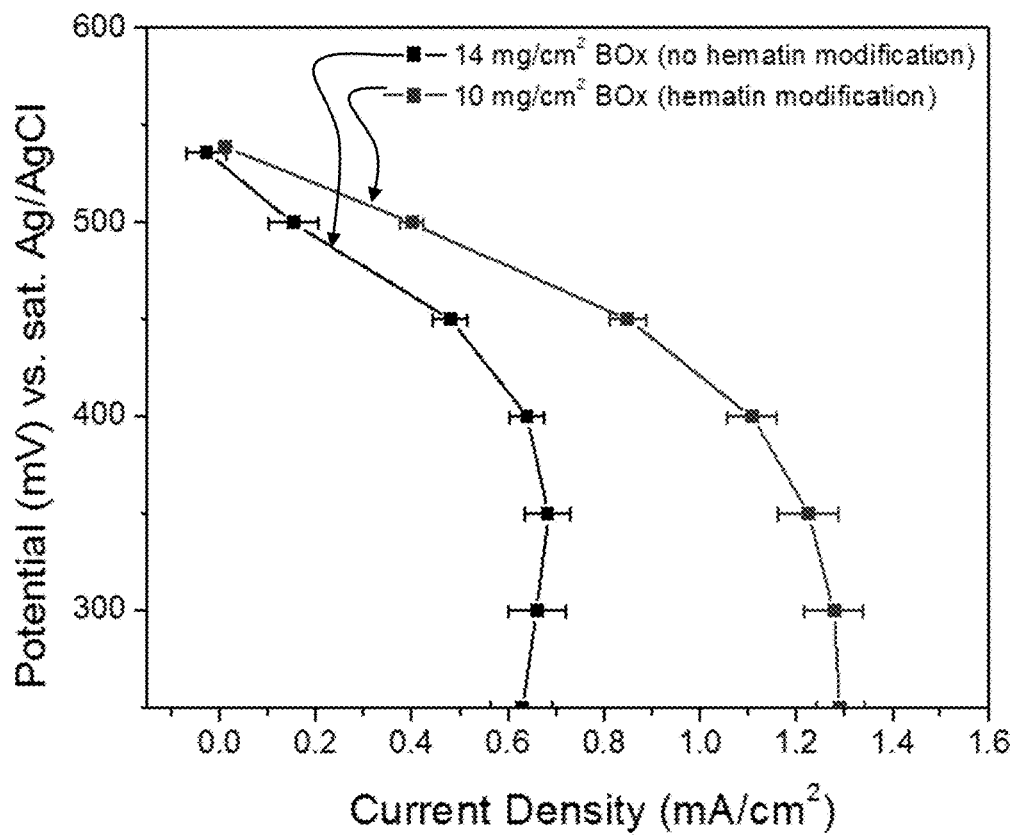
FIG. 8 shows data for representative step potential curves for 14 $mg/cm^2$ BOx cathodes with no hematin modification compared to hematin-modified BOx cathodes with 10 $mg/cm^2$ BOx loading.

FIG. 8 compares the performance of an optimized BOx cathode without hematin modification to an optimized BOx cathode with hematin modification. At 300 mV, the hematin-modified BOx cathodes performed 85% better than the non-hematin modified BOx cathodes. Thus, the benefits of the hematin-modified BOx cathodes not only include increased current density output, but also include the added benefit of cheaper cathode preparation costs due to the 28.6% reduction in BOx loading. FIG. 8 shows data for representative step potential curves for 14 mg/cm' BOx cathodes with no hematin modification compared to hematin-modified BOx cathodes with 10 mg/cm' BOx loading.

Figure 9A:
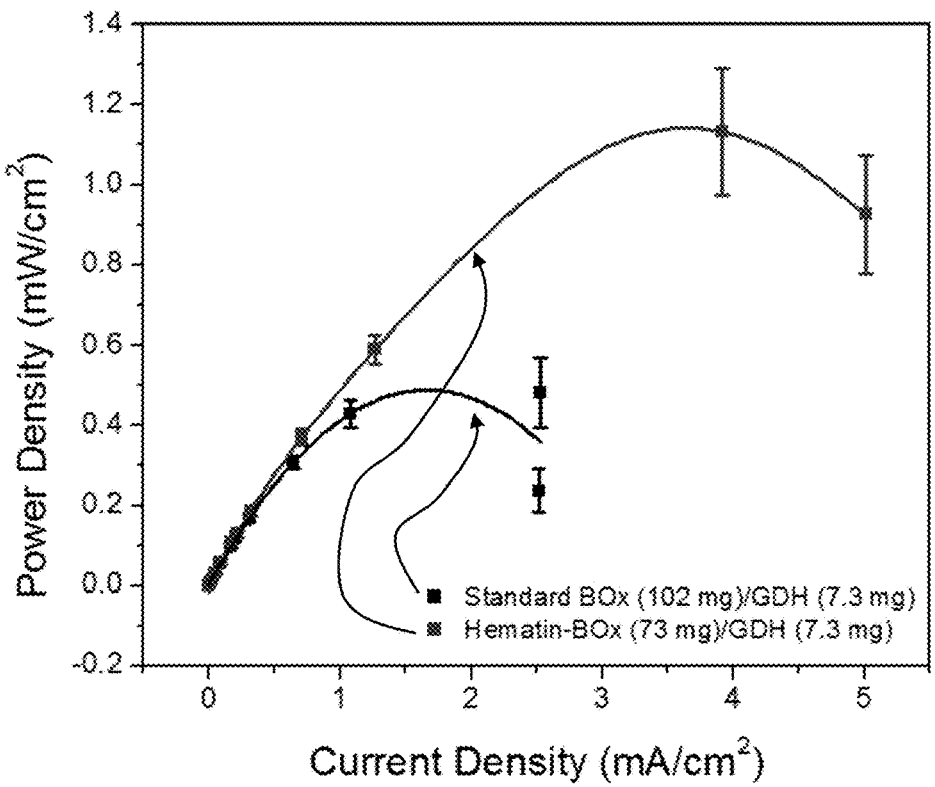
FIG. 9A shows data for representative power density curves for a standard BOx/GDH fuel cell compared to a hematin-BOx/GDH fuel cell tested with 0.05 M glucose/10 mM NAD fuel.
Figure 9B:
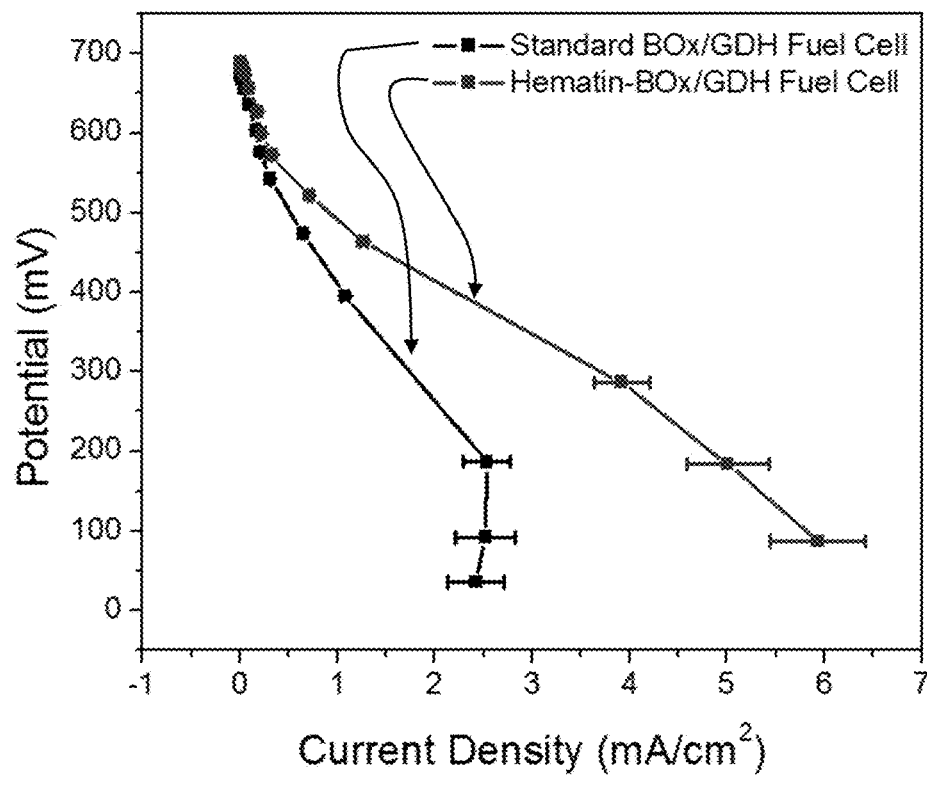
FIG. 9B shows data for representative current density curves for a standard BOx/GDH fuel cell compared to a hematin-BOx/GDH fuel cell tested with 0.05 M glucose/10 mM NAD fuel.

After optimizing BOx loading on the hematin-modified air breathing cathodes, complete fuel cell testing was conducted to compare non-hematin BOx cathodes (standard) to hematin-BOx cathodes. BOx cathodes (2) were paired with GDH anodes to form a complete enzymatic fuel cell. Power density and current density curves were generated for each fuel cell type (FIGS. 9A-9B). The loading for GDH was 1 mg/cm$^2$ (minimal loading). The fuel used for testing was 0.05 M glucose with 10 mM NAD. Optimal loading was used for both the non-hematin BOx cathodes, and the hematin BOx cathodes. Testing was conducted in triplicate. The average peak power density for the hematin-BOx/GDH fuel cells exceeded 1.0 mW/cm$^2$. The hematin-BOx/GDH fuel cells performed over 2 times better than the non-hematin BOx/GDH fuel cells in terms of peak power and current densities. The hematin-modified BOx air breathing cathodes will now serve as the primary BOx cathodes for all future work. FIG. 9A shows data for representative power density curves for a standard BOx/GDH fuel cell compared to a hematin-BOx/GDH fuel cell tested with 0.05 M glucose/10 mM NAD fuel. FIG. 9B shows data for representative current density curves for a standard BOx/GDH fuel cell compared to a hematin-BOx/GDH fuel cell tested with 0.05 M glucose/10 mM NAD fuel.

Figure 10A:
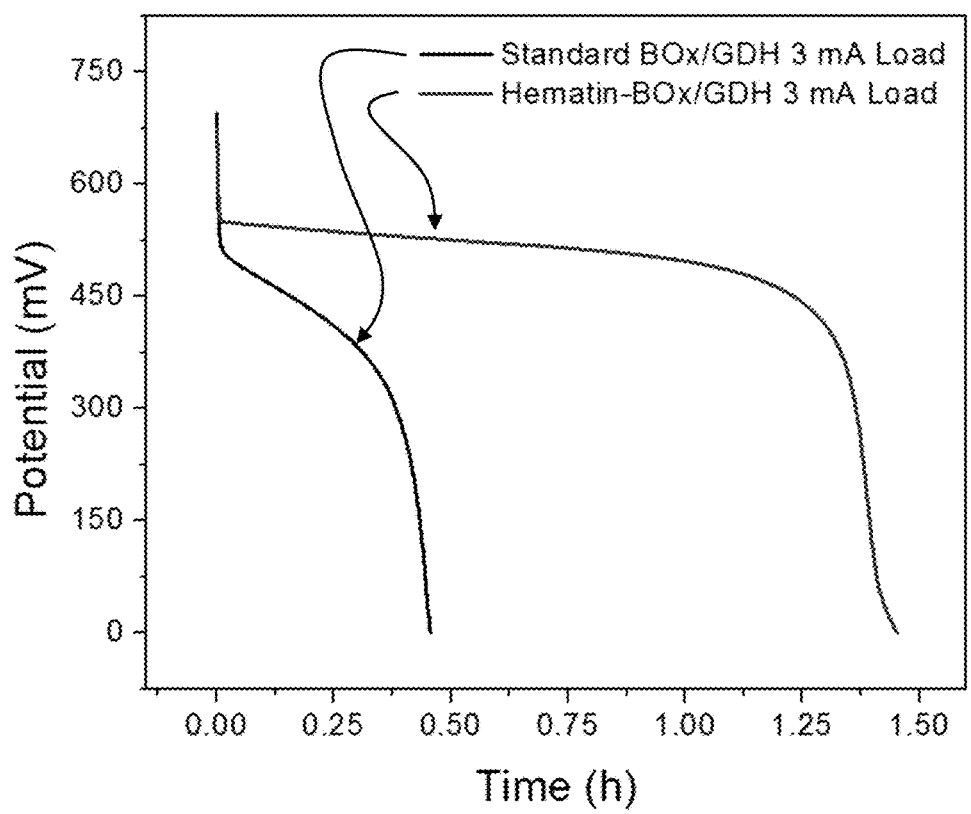
FIG. 10A shows data for representative discharge curves comparing a standard BOx/GDH fuel cell to a hematin-BOx/GDH fuel cell under a constant current load of 3 mA.
Figure 10B:
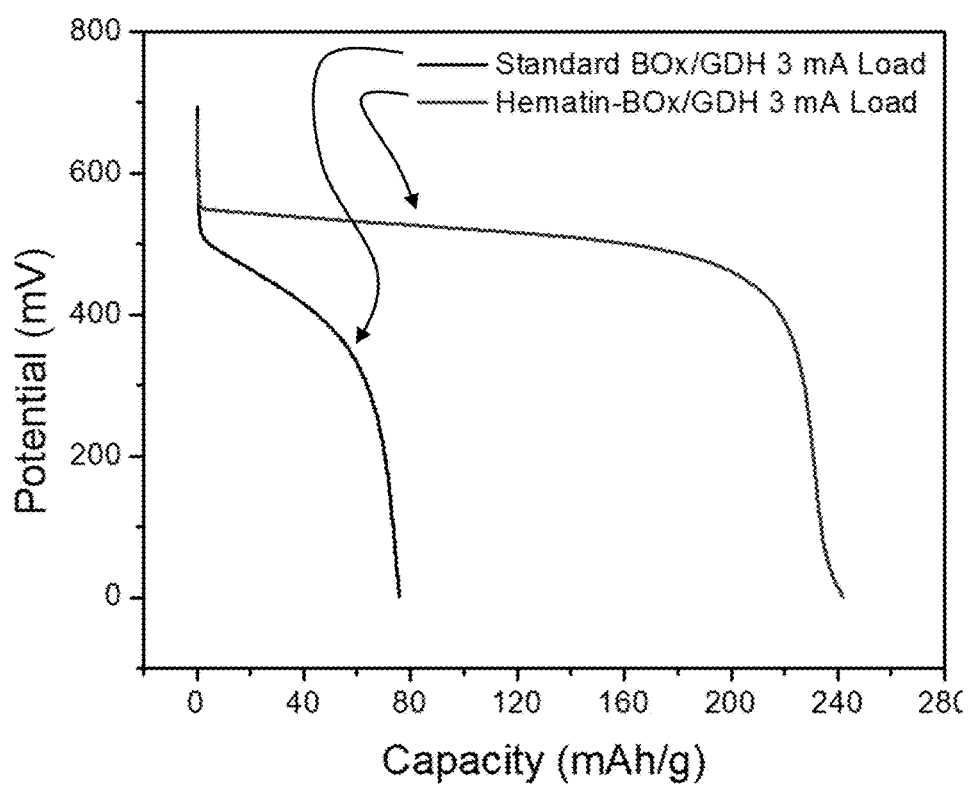
FIG. 10B shows data for representative capacity curves comparing a standard BOx/GDH fuel cell to a hematin-BOx/GDH fuel cell under a constant current load of 3 mA.

In addition to generating power and current density curves for BOx (2)/GDH fuel cells. The fuel cells were also tested under constant current loads to obtain capacity and energy density data. The standard BOx (2)/GDH and hematin-BOx (2)/GDH fuel cells were tested under a 3 mA current load. Testing was completed under batch mode initially to compare the two different fuel cell types. The fuel cells were tested with 0.05 M glucose/10 mM NAD fuel. Representative discharge and capacity curves for the constant current load discharge test under batch mode conditions are displayed in FIGS. 10A-10B. FIG. 10A shows data for representative discharge curves comparing a standard BOx/GDH fuel cell to a hematin-BOx/GDH fuel cell under a constant current load of 3 mA. FIG. 10B shows data for representative capacity curves comparing a standard BOx/GDH fuel cell to a hematin-BOx/GDH fuel cell under a constant current load of 3 mA.

On average, the hematin-BOx (2)/GDH fuel cells ran for 3 times longer than the non-hematin-BOx (2)/GDH fuel cells (Table 1). The average capacity and energy density for the hematin-BOx (2)/GDH fuel cells were 216.67 mAh/g and 102.41 mWh/g, respectively. The average energy density for the hematin-BOx (2)/GDH fuel cells was 4 times higher than the energy density for the non-hematin BOx (2)/GDH fuel cells.

TABLE 1

Summary of results for various fuel cells tested under batch mode.
Batch Mode Fuel Cell Testing

| Fuel Cell System | Current Load (mA) | Glucose Per 2 ml Cell (g) | Average Runtime (h) | Capacity-Glucose mAh | Capacity-Glucose mAh/g | Average Energy Density-Glucose (mWh/g) |
|---|---|---|---|---|---|---|
| Standard/non-Hematin BOx(2)/GDH | 3.0 | 0.018 | 0.37 | 1.11 | 61.67 | 23.15 |
| Hematin-BOx(2)/GDH | 3.0 | 0.018 | 1.30 | 3.9 | 216.67 | 102.41 |

Figure 11A:
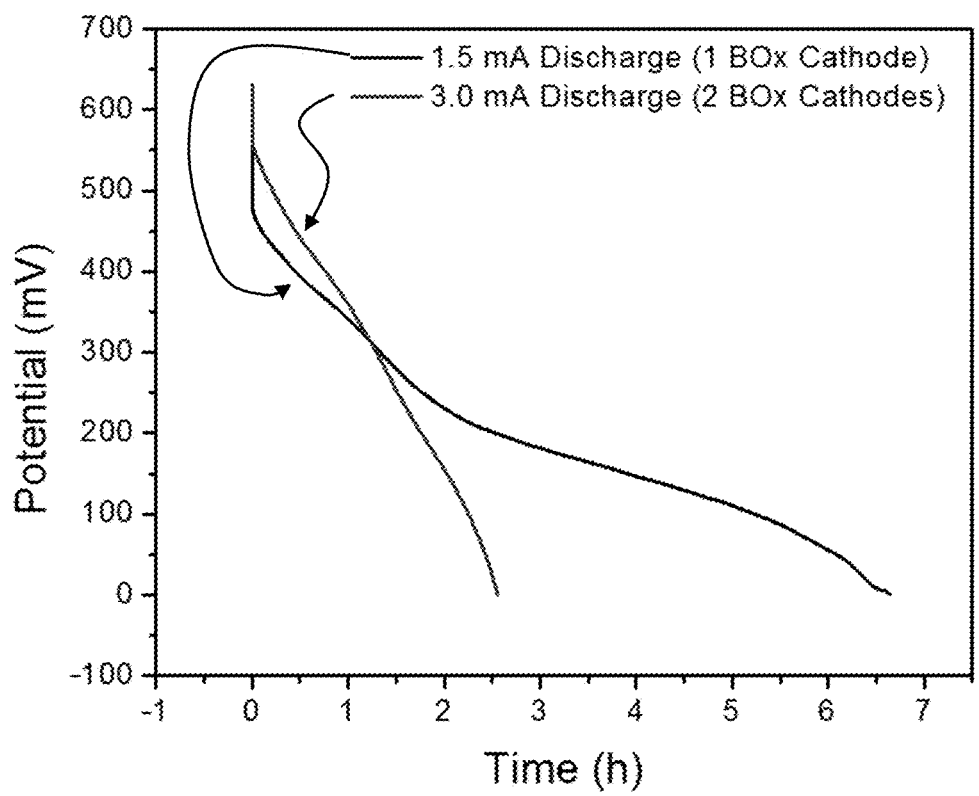
FIG. 11A shows data for representative discharge curves comparing a hematin-BOx/GDH fuel cell under a 1.5 mA load to a BOx (2)/GDH fuel cell under a 3.0 mA load.
Figure 11B:
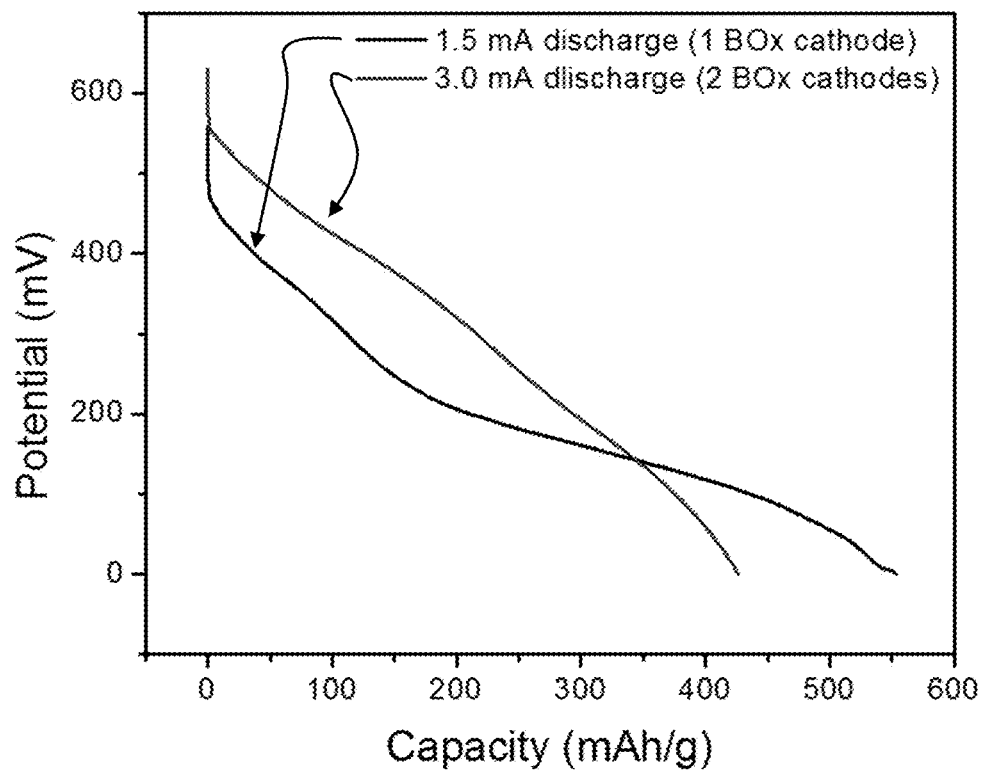
FIG. 11B shows data for representative capacity curves comparing a hematin-BOx/GDH fuel cell under a 1.5 mA load to a BOx (2)/GDH fuel cell under a 3.0 mA load.

Flow-through mode constant discharge tests were conducted with hematin-BOx/GDH fuel cells. Under flow-through mode, the 0.05 M glucose was constantly flowed into the 2 ml capacity fuel cells. The mediator for the GDH anode, NAD, was immobilized onto the anode surface following standard procedures. The fuel cells were either tested with 2 BOx cathodes or 1 BOx cathode under a 3.0 mA or 1.5 mA load, respectively. Representative discharge and capacity curves for the flow-through study are displayed in FIGS. 11A and 11B. FIG. 11A shows data for representative discharge curves comparing a hematin-BOx/GDH fuel cell under a 1.5 mA load to a BOx (2)/GDH fuel cell under a 3.0 mA load. FIG. 11B shows data for representative capacity curves comparing a hematin-BOx/GDH fuel cell under a 1.5 mA load to a BOx (2)/GDH fuel cell under a 3.0 mA load.

Table 2 summarizes the results for the hematin-BOx/GDH flow-through study. On average, the fuel cells with a single BOx cathode ran for over 2 times longer than the fuel cells with 2 BOx cathodes. The capacity for both fuel cell types exceeded 390 mAh/g.

Figure 12A:
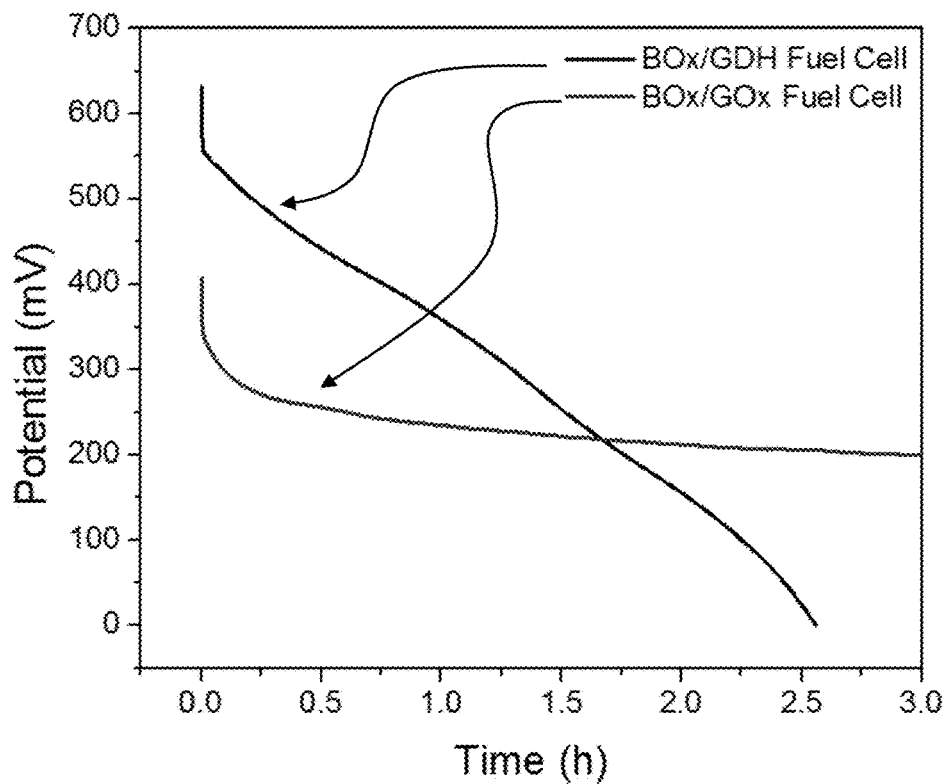
FIG. 12A shows data for representative discharge curves comparing a hematin-BOx/GOx fuel cell to a BOx/GDH fuel cell under a 3.0 mA load.
Figure 12B:
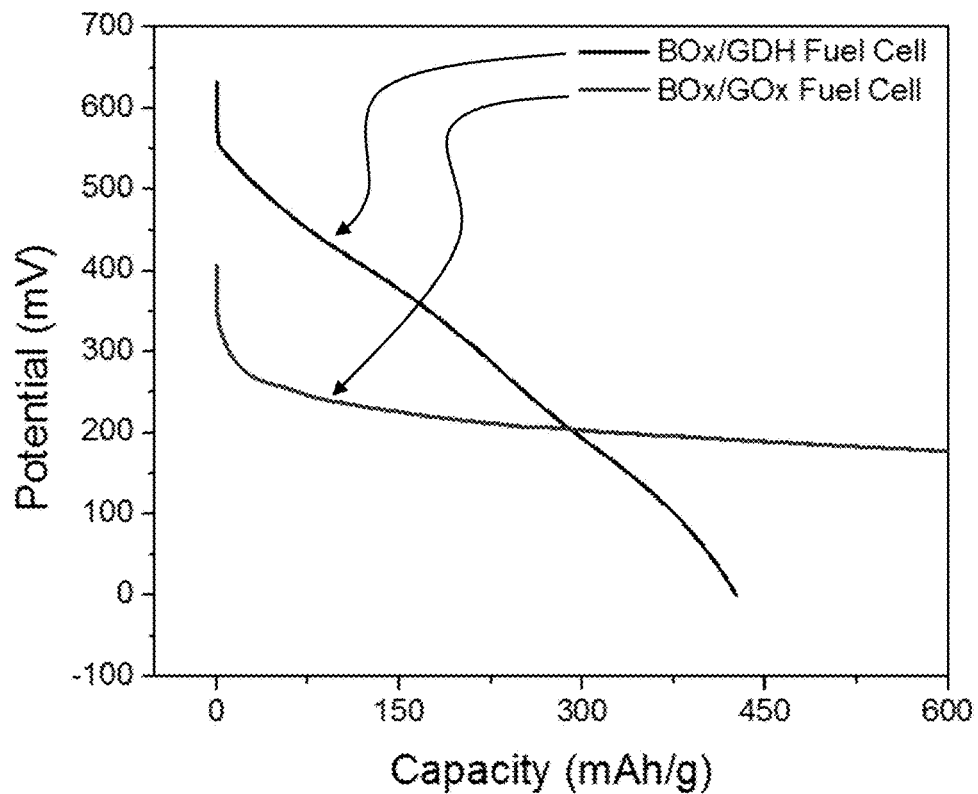
FIG. 12B shows data for representative capacity curves comparing a hematin-BOx/GOx fuel cell to a BOx/GDH fuel cell under a 3.0 mA load.

FIGS. 12A and 12B compare the performance of flow-through BOx/GDH fuel cells to BOx/GOx fuel cells. While the BOx/GOx fuel cells ran for longer than the BOx/GDH fuel cells under flow-through mode, the BOx/GDH fuel cells were able to maintain a potential above 300 mV for much longer than the BOx/GOx fuel cells. When the fuel cells reach 300 mV, the capacity for the BOx/GOx fuel cell was less than 100 mAh/g, while the capacity for the BOx/GDH fuel cells exceeded 150 mAh/g. The extended runtime for the BOx/GOx fuel cells was most likely due to the constant supply of glucose and mediator (HQ). The shorter runtime for the BOx/GDH fuel cells was most likely due to the slow redox of NADH to NAD. Due to the high cost of the mediator, NAD was immobilized on the GDH anode for flow-through testing. Although the GDH anode was modified with the redox polymer, polymethylene green, to improve the NAD/NADH redox, the mediator redox step progressed slowly, which in turn led to lower GDH anode performance. However, while performance of the flow-through BOx/GDH fuel cells was limited by the GDH mediator redox, glucose capacity still exceeded 300 mAh/g. FIG. 12A shows data for representative discharge curves comparing a hematin-BOx/GDH fuel cell under a 1.5 mA load to a BOx (2)/GDH fuel cell under a 3.0 mA load. FIG. 12B shows data for representative capacity curves comparing a hematin-BOx/GDH fuel cell under a 1.5 mA load to a BOx (2)/GDH fuel cell under a 3.0 mA load.

Preparation of a hematin modified BOx cathode can include EDC-NHS coupling of hematin to a substrate, and then drying. PBSE is attached to MWCNTs and DMY-Carb is attached to BOx, and then the PBSE is coupled to the DMY-Carb through the tertiary nitrogen.

Hematin modified electrodes were prepared as follows. Air breathing cathodes were fabricated. Briefly, teflonized carbon black powder (35% teflonization and 50% teflonization, XC35 and XC50) and MWCNTs paper (Buckeye Composites) were hydraulically pressed for 5 minutes at 1000 psi. A 10 mM hematin solution was prepared by

TABLE 2

Summary of results for flow-through hematin-BOx/GDH fuel cells tested with 1 or 2 cathodes.
BOx/GDH (Immobilized NAD) Flow-Through Results

| Fuel Cell System | Current Load (mA) | Glucose Per 2 ml Cell (g) | Average Runtime (h) | Capacity-Glucose mAh | Capacity-Glucose mAh/g | Average Energy Density-Glucose (mWh/g) |
|---|---|---|---|---|---|---|
| BOx(2)/GDH | 3.0 | 0.018 | 2.38 | 7.14 | 396.67 | 118.89 |
| BOx(1)/GDH | 1.5 | 0.018 | 5.49 | 8.24 | 457.78 | 90 | mixing 10 mM hematin (prepared in DMSO) into 100 mM sodium hydroxide (NaOH) solution. The as prepared solution was sonicated for 1 hour.

Hematin modified electrodes with BOx/EDC-NHS coupling was performed as follows. The air breathing BOx/hematin electrodes were successively modified with additional components: 1-(3-Dimethylaminopropyl)-3'ethylcarbodiimide Hydrochloride (EDC) and N-Hydroxysuccinimide (NHS). Hematin solution (10 mM) was prepared as described in a previous section. After 1 hour sonication, 55.2 mg of EDC and NHS was added and 761 μL of a prepared solution mixture was deposited onto the buckypaper layer (7.3 cm$^2$) of the pressed air breathing cathode. The electrodes were left to dry for 4 hours at room temperature.

Hematin/EDC-NHS modified electrodes with BOx were prepared as follows. Preparation of BOx ink: 2 wt % MWCNT ink solution was prepared by dissolving 4:1 ratio of water to ethanol (by weight) and added to 100 mg MWCNTs (10-20 nm). The prepared mixture was subjected to sonication for 1 hour in an ice bath with vortexing every 20 min interval time. 15 μL of 300 mM DMY-Carb (in DMSO) and 525 μL of stock solution of 2% MWCNT ink were mixed, vortexed and incubated for 1 hour. This was followed by addition of 15 μL of 300 mM PBSE (in DMSO) and incubation for 1 hour. BOx (73 mg) was weighed and added to MWCNT ink and incubated again for 1 hour at room temperature. Then 761 μl of ink was then deposited on the pre-wetted buckeye paper of the air breathing cathode modified with hematin respectively. Control electrodes were prepared by drop casting ink onto unmodified air breathing cathodes. Following ink deposition, a chemical vapor deposition of tetramethyl orthosilicate (TMOS) was performed by sealing cathodes in a petri dish containing small caps filled with water and TMOS. The petri dish remained sealed for 5 minutes before discarding the TMOS. Cathodes were then stored at 4° C. overnight.

Anode Experimental

Fuel cell testing was conducted employing a gold nanoparticle (AuNP) based anode for glycerol oxidation. Initial tests were conducted with prussian blue (PB) based cathodes. PB cathodes were employed to preserve bilirubin oxidase (BOx) stock; however, BOx cathodes may be used with these anodes. The following procedure was used to prepare the AuNP anodes: 15 mg of 10% platinum on carbon black powder (e.g., Pt—XC72 Vulcan) was mixed with 1 mL of AuNPs and 6 μL of polytetrafluoroethylene (PTFE). The XC72 Vulcan can be referred to herein as XC72, which is a conductive carbon black. The solution was thoroughly mixed using vortexing and sonication. The AuNP/Pt—XC72 solution (1 ml), which can be considered to be a conductive ink, was drop casted onto each inner side of a 5.2 cm$^2$ carbon felt electrode. The carbon felt electrode was plasma cleaned prior to the conductive ink deposition. The electrodes were allowed to dry overnight at room temperature. The PB cathodes were prepared following a standard procedure.

The fuel cell tests with the AuNP/Pt—XC72 anode (also referred herein as the AuNP anode) were conducted with 2 M KOH electrolyte with a Nafion membrane as a separator. However, enzymes cannot serve as efficient catalysts in such alkaline environments. For this reason, tests were conducted to determine if the AuNP anode can be modified to work under neutral pH conditions. Modifying the acid-base properties of the AuNP anode can allow for the AuNP anode to work under enzyme-friendly pH conditions. This would allow for the AuNPs to be paired with the enzyme, oxalate decarboxylase (OxDc), for complete oxidation of glycerol to $CO_2$. In addition, the AuNP anode being useful under neutral pH conditions allows for the AuNP anode to be paired with a BOx cathode in a membrane-less fuel cell (e.g., fuel cell devoid of a membrane).

It was found that the AuNP anode can be used for the polyol (e.g., glycerol) based fuel cell. The AuNP anode was shown to work well when the highly alkaline, 2 M potassium hydroxide (KOH) served as the electrolyte. However, since the bilirubin oxidase (BOx) cathode or other enzymatic cathode requires a more neutral electrolyte to preserve the function of the enzyme, the AuNP anode can be configured to oxidize glycerol in neutral buffer solutions.

Figure 13A:
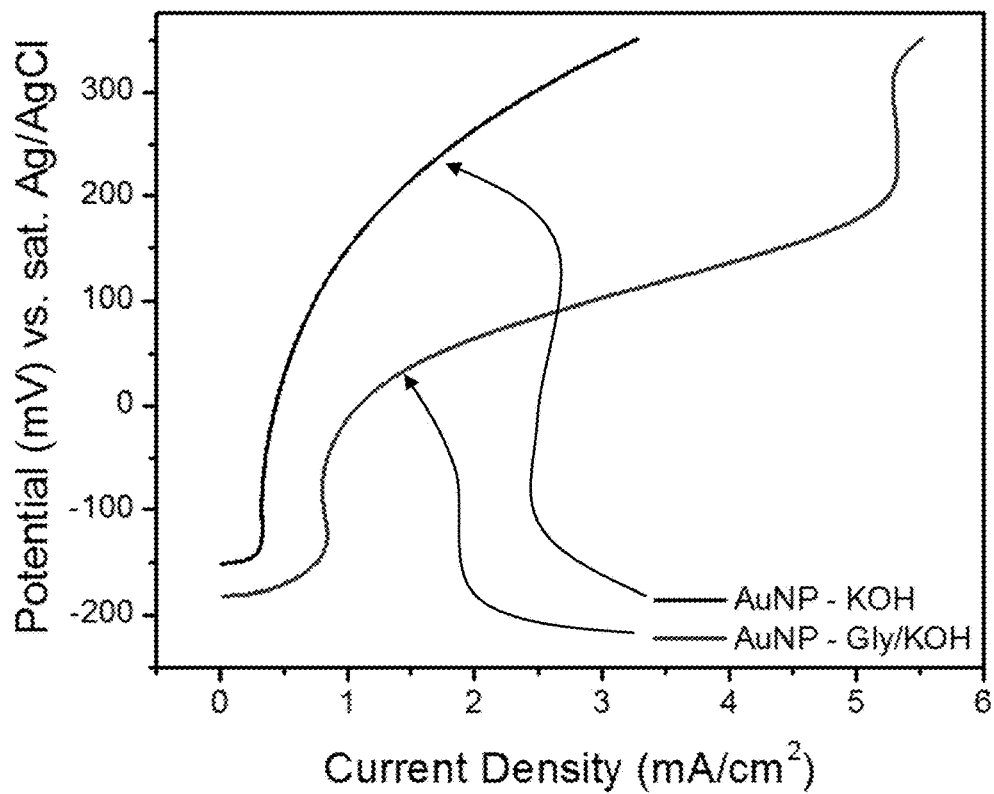
FIG. 13A shows the data for AuNP anode tested in 2 M KOH or 1 M glycerol/2 M KOH.
Figure 13B:
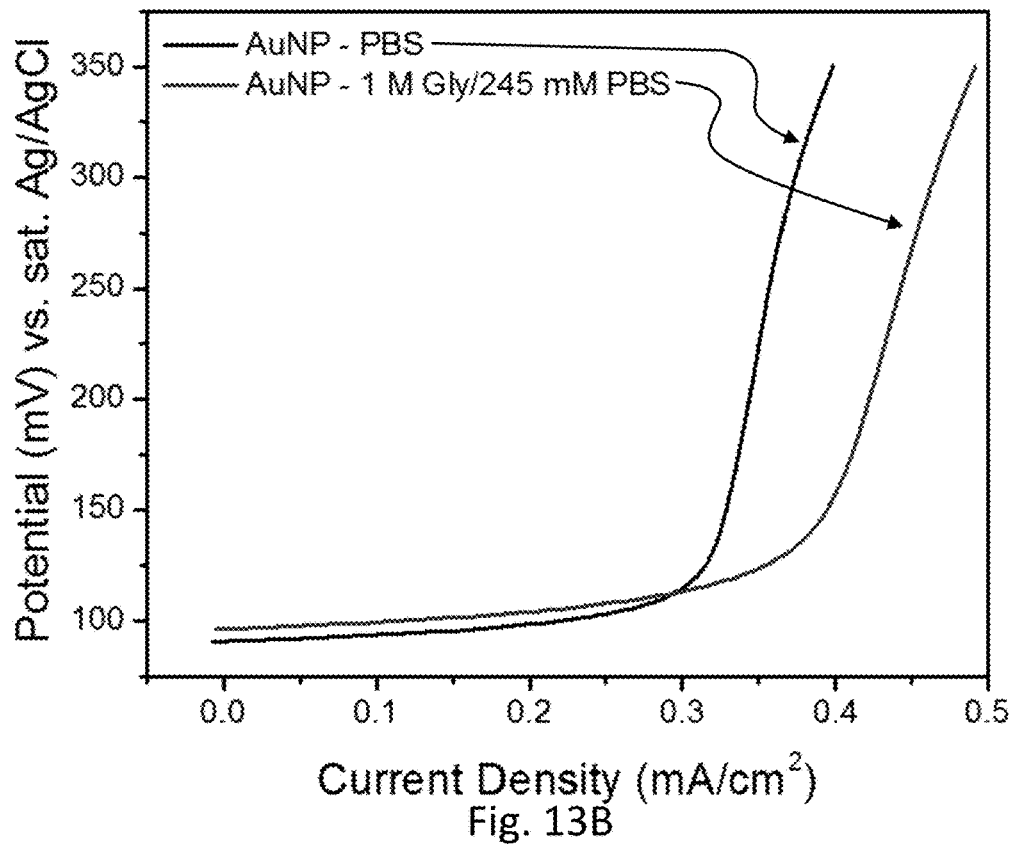
FIG. 13B shows the data for AuNP anode tested in 245 mM PBS or 1 M glycerol/245 mM PBS.

Studies were performed for comparing the AuNP anode performance in alkaline and neutral environments. Buckypaper electrodes (1 cm$^2$) were rinsed with IPA and water. Then 50 of AuNP (e.g., without Pt—XC72) was drop casted onto the electrodes. The electrodes were allowed to dry at room temperature prior to testing. The electrodes were tested in a three electrode cell with a platinum counter and a silver/silver chloride (Ag/AgCl) reference electrode. Control testing was conducted in either 10 ml of 2 M KOH (alkaline) or 245 mM sodium phosphate buffer, pH 7 (PBS buffer) (neutral). Sample testing was conducted in either 10 ml 1 M glycerol/2 M KOH or 1 M glycerol/PBS buffer. Linear sweep voltammetry (LSV) was employed to generate polarization curves. The potential was scanned from the OCV to 500 mV at a scan rate of 10 mV/s. The results for this study can be viewed in FIGS. 13A and 13B. There was a slight increase in current density when the AuNP anode was tested in 1 M glycerol/PBS buffer, but performance was much lower than the performance observed when 1 M glycerol/2 M KOH was employed as the fuel. In addition, the OCV was very high (~100 mV) when the anode was tested in a neutral electrolyte. For this reason, optimization studies were conducted to improve an AuNP anode performance in a PBS buffer. FIG. 13A shows the data for an AuNP anode tested in 2 M KOH or 1 M glycerol/2 M KOH. FIG. 13B shows the data for AuNP anode tested in 245 mM PBS or 1 M glycerol/245 mM PBS.

Figure 14:
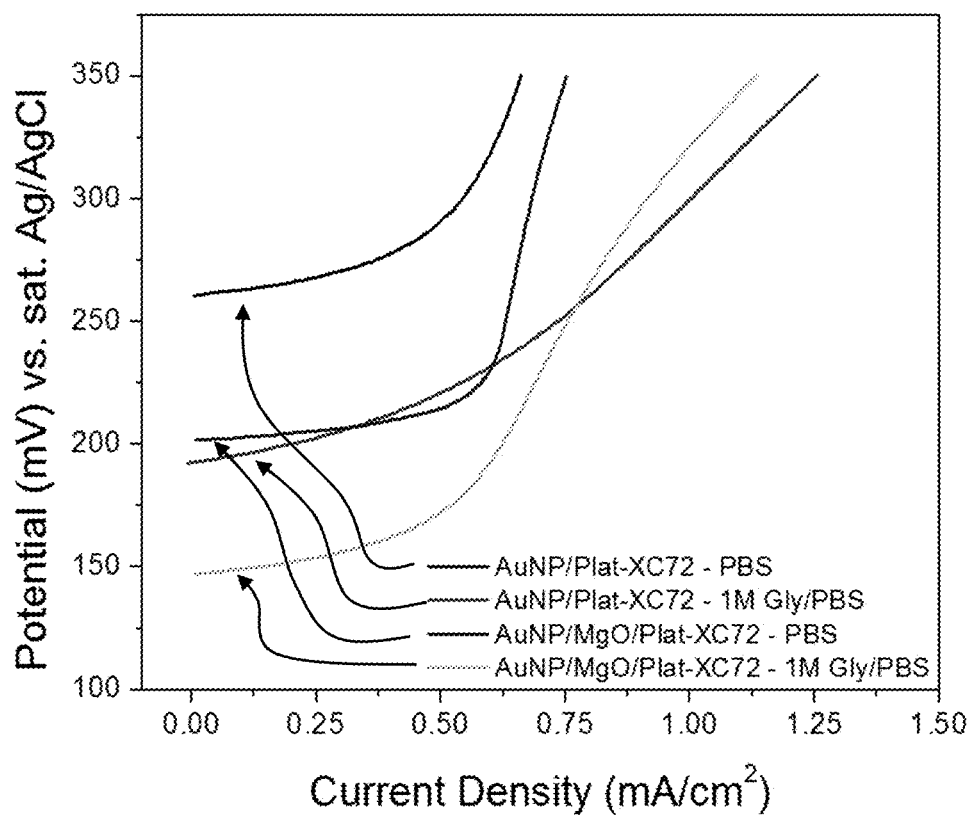
FIG. 14 shows the AuNP/Pt—XC-72 anodes tested in PBS or 1 M glycerol/PBS, and AuNP/MgO/Pt—XC72 anodes tested in PBS or 1 M glycerol/PBS.

To determine if the incorporation of Pt—XC72 could increase AuNP anode performance in PBS buffer, AuNP/Pt—XC72 buckypaper anodes were prepared. The AuNP/Pt—XC72 ink solution was prepared by mixing 50 μl of AuNPs with 1.17 mg of Pt—XC72 and 0.33 μl of polytetrafluoroethylene (PTFE). The solution was drop casted onto a 1 cm$^2$ piece of buckypaper, and allowed to dry prior to testing. In addition, a similar anode was prepared with MgO (1.17 mg) also incorporated into the ink solution with the AuNP/Pt—XC72 (e.g., AuNP/MgO/Pt—XC72). MgO has been shown to improve the catalytic activity of AuNPs under base free conditions. FIG. 14 displays the results for both the AuNP/Pt—XC72 anode, and the AuNP/MgO/Pt—XC72 anode. When MgO and Pt—XC72 were incorporated into the AuNP anode, the current densities exceeded 1 mA/cm$^2$ at 350 mV. As seen in FIG. 13A, the current densities were less than 0.5 mA/cm$^2$ when AuNPs were employed alone. While the current densities were promising, the OCV was still high for the AuNP/Pt—XC72 and AuNP/MgO/Pt—XC72 based anodes. FIG. 14 shows the AuNP/Pt—XC-72 anodes tested in PBS or 1 M glycerol/PBS, and AuNP/MgO/Pt—XC72 anodes tested in PBS or 1 M glycerol/PBS.

Figure 15:
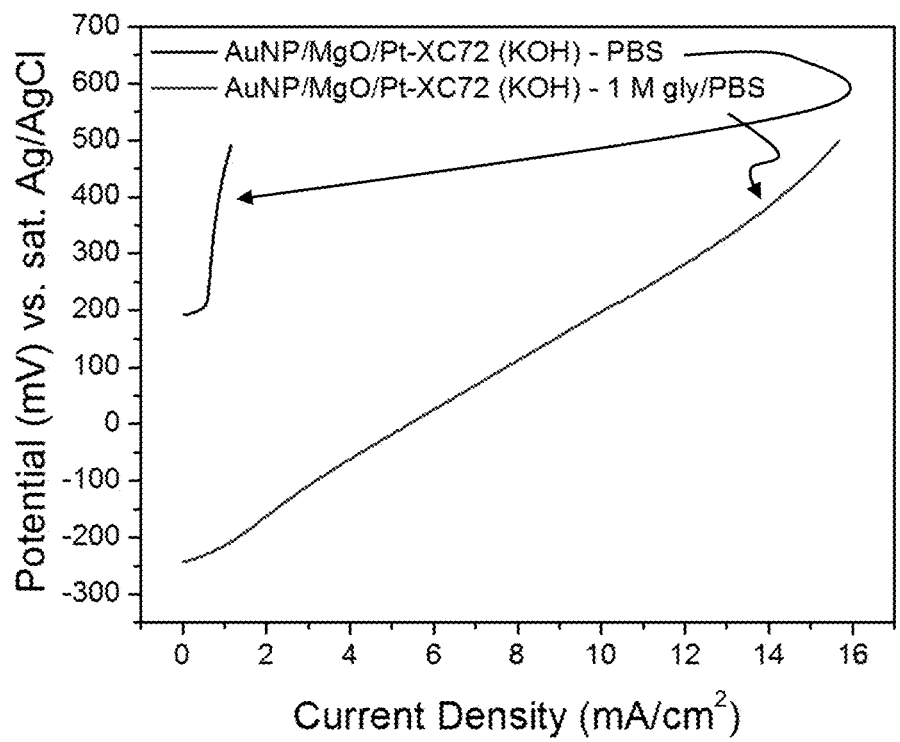
FIG. 15 shows AuNP/MgO/Pt—XC-72 anodes tested in PBS or 1 M glycerol/PB S.

In order to further improve performance of the AuNP anode, a KOH pretreatment was employed. This provides for an alkaline microenvironment near the AuNP particles or at the surfaces thereof. Buckypaper electrodes were rinsed with IPA and water prior to being placed into a three electrode cell with 10 ml of 2 M KOH. A constant load of 1.2 V was applied to the buckypaper electrode for 5 minutes. Afterwards, the electrodes were rinsed with water and allowed to dry at room temperature prior to depositing AuNP/MgO/Pt—XC72 ink onto the electrode surface. The electrodes were allowed to dry before being tested in either PBS (control) or 1 M glycerol/PBS buffer (sample). At 350 mV (FIG. 15), the current density exceeded 10 mA/cm$^2$ when the anode was tested in the sample fuel. The OCV also dropped significantly after the KOH treatment, but only when the anode was tested in the sample fuel. In the control fuel, the OCV was still greater than 100 mV. FIG. 15 shows AuNP/MgO/Pt—XC-72 anodes tested in PBS or 1 M glycerol/PBS.

Since the addition of Pt—XC72 led to over a 2× increase in AuNP anode performance, the Pt—XC72 was selected as the lead catalyst for glycerol oxidation. All testing was conducted in a three electrode cell with 10 ml of 1 M glycerol/PBS buffer.

Figure 16A:
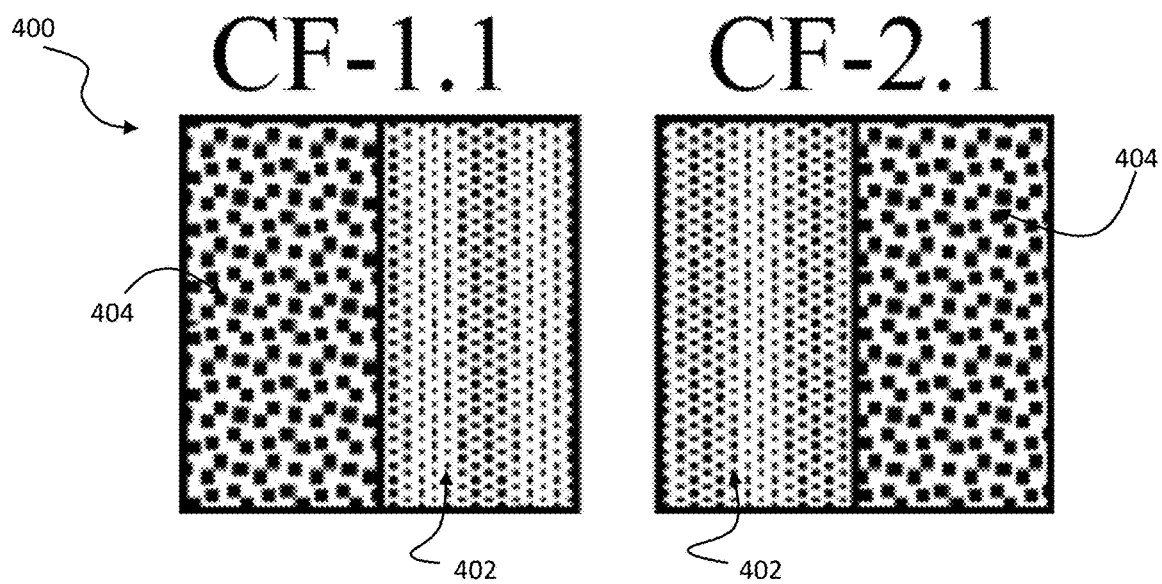
FIG. 16A provides a schematic representation of the band method employed for drop casting AuNP/MgO/Pt—XC72 solution and OxDc ink onto carbon felt electrodes.

Testing was conducted with the incorporation of Oxalate decarboxylase (OxDc) into the metallic based anode using two different methods: band method and sandwich method. The band method involved drop casting 730 μl AuNP/MgO/Pt—XC72 onto half of each piece of carbon felt, and 400 μl OxDc onto the other half of each piece of carbon felt. When the fuel cell was assembled, the AuNP/MgO/Pt—XC72 side of CF-1.1 was in contact with the AuNP/MgO/Pt—XC72 side of CF-2.1 (FIG. 16A). As shown, anode 400 includes the substrate being carbon felt, having the AuNP composition 402 on one half of the anode substrate and OxDc composition 404 on the other half of the anode substrate. The band method allowed for the incorporation of OxDc into the metallic catalyst based anode without mixing the OxDc directly into the AuNP metallic ink. FIG. 16A provides a schematic representation of the band method employed for drop casting AuNP/MgO/Pt—XC72 solution and OxDc ink onto carbon felt electrodes.

Figure 16B:
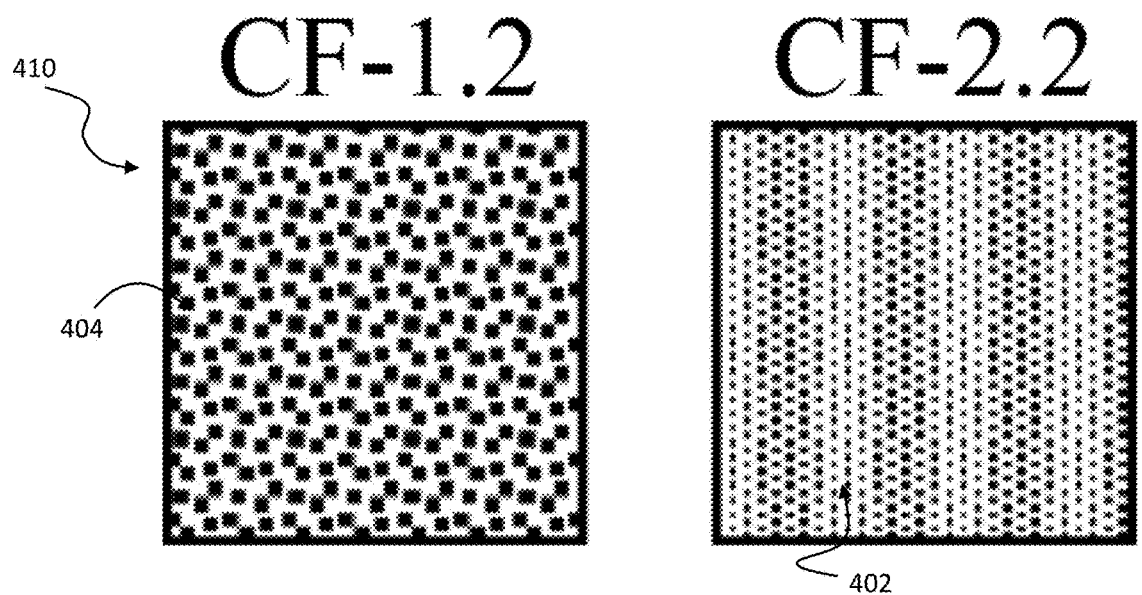
FIG. 16B provides a schematic representation of the sandwich method employed for drop casting AuNP/MgO/Pt—XC72 solution and OxDc ink onto carbon felt electrodes.

The sandwich method involved drop casting 1460 μl AuNP/MgO/Pt—XC-72 onto one piece of carbon felt and 800 μl OxDc onto the other piece of carbon felt (FIG. 16B). As shown, anode 410 includes a first substrate being carbon felt having the AuNP composition 402 and a second substrate being carbon felt having the OxDc composition 404. When the fuel cell was assembled, the OxDc ink on CF-1.2 was in direct contact with the AuNP/MgO/Pt—XC72 on CF-2.2. FIG. 16B provides a schematic representation of the sandwich method employed for drop casting AuNP/MgO/Pt—XC72 solution and OxDc ink onto carbon felt electrodes.

Fuel cell tests of the AuNP/MgO/Pt—XC-72/OxDc anodes with bilirubin oxidase (BOx, Amano, 2.67 U/mg) cathodes were conducted in the standard 7.3 cm$^2$ array hardware (~1 ml volume). Air breathing hematin-modified BOx (10 mg/cm$^2$) cathodes were prepared following standard procedures (see the incorporated reference having attorney docket number C1478.10028US01, Ser. No. 62/626,529, which attorney docket number is to be replaced by the serial number of the provisional application once filed on the same date herewith). The following procedure was employed to prepare the hybrid anodes.

Generally, carbon felt is treated with 2 M KOH under 1.2 V to yield hydroxyl groups on the surface and then metal nanocomposite Pt/Vulcan/AuNP/MgO is applied to the hydroxyl groups only on one side or one portion of a surface of the carbon felt. Then, carbon nanotubes that have PEI—COOH are treated with EDGE to link the carbon nanotubes to the OxDC from the enzymatic nanocomposite that is applied to the other side or remainder portion of the surface of the felt surface.

In the process, 7.3 cm$^2$ pieces of carbon felt (0.125 inch thick) were cut out, and sliced in two (lengthwise). The carbon felt electrodes were plasma cleaned on high for 5 minutes. Afterwards, the electrodes were rinsed with IPA and water (excess liquid removed with paper towel). A three-electrode cell with 15 ml of 2 M KOH was set-up. A potential load of 1.2 V was applied to the carbon felt electrodes for 10 min. Then the carbon felt electrodes were rinsed with water (excess liquid removed with paper towel). The electrodes were stored at room temperature for at least 2 hours before ink deposition. The AuNP/MgO/Pt—XC72 ink was prepared by mixing Pt—XC72 (45.6 mg) and MgO (91.25 mg) with AuNPs (1.825 ml). After sonicating the solution for 30 seconds, 12.2 μl of PTFE was added to the AuNP solution. After vortexing the solution, the metallic ink was drop casted onto the carbon felt electrodes following either the band or sandwich method. The OxDc ink was prepared by adding 50 μl of OxDc to 750 μl of 10% EGDE and CFDRC Ink (e.g., aqueous solution of SWCNT conductive agent, PEI binding agent, and NHS/EDC as crosslinkers). The OxDc ink solution was vortexed, and then drop casted onto the carbon felt electrodes following either the band or sandwich method.

Figure 17A:
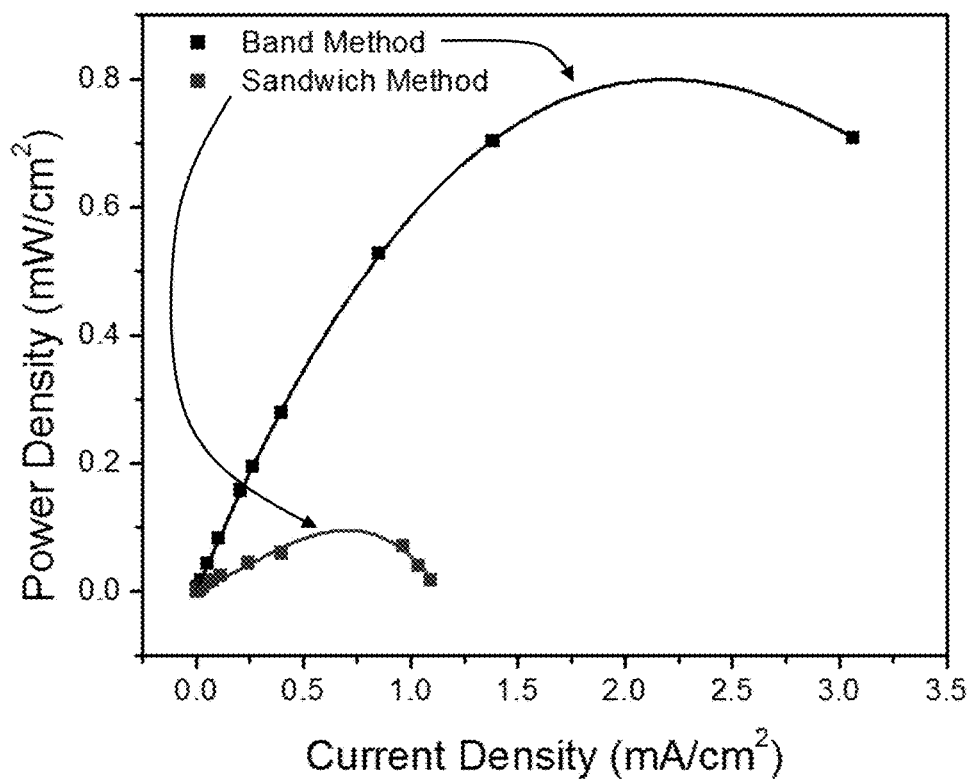
FIG. 17A provides data showing the representative power curve for glycerol fuel cells containing a BOx cathode and a band method AuNP/MgO/Pt—XC72/OxDc anode or a sandwich method AuNP/MgO/Pt—XC72/OxDc anode. \
Figure 17B:
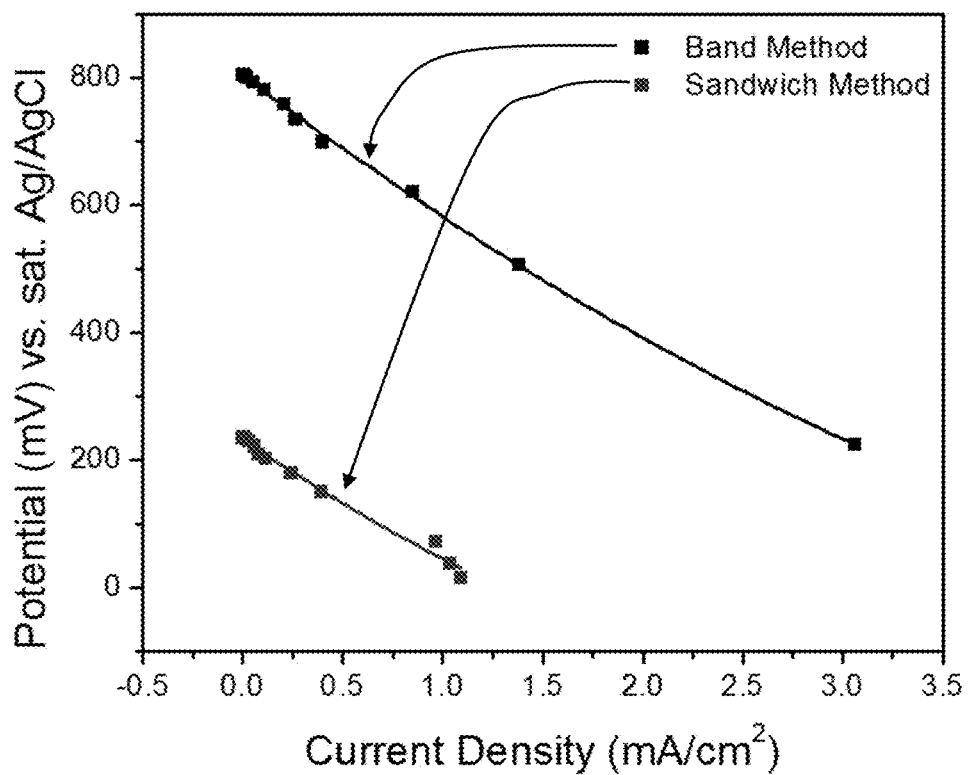
FIG. 17B provides data showing the representative current density curves for glycerol fuel cells containing a BOx cathode and a band method AuNP/MgO/Pt—XC72/OxDc anode or a sandwich method AuNP/MgO/Pt—XC72/OxDc anode.

The fuel cells were tested with 100 mM glycerol fuel. The fuel cells containing the band method hybrid anodes performed significantly better than the fuel cells containing the sandwich method hybrid anodes (FIGS. 17A and 17B). The peak power density was 8 times higher when a band method hybrid anode was employed. The OCV was also very low for the fuel cell containing the sandwich method hybrid anode. The exact reason for the low OCV was unknown. Normally, the KOH treatment of the carbon felt combined with glycerol fuel leads to an increase in the OCV. FIG. 17A provides data showing the representative power curve for glycerol fuel cells containing a BOx cathode and a band method AuNP/MgO/Pt—XC72/OxDc anode or a sandwich method AuNP/MgO/Pt—XC72/OxDc anode. FIG. 17B provides data showing the representative current density curves for glycerol fuel cells containing a BOx cathode and a band method AuNP/MgO/Pt—XC72/OxDc anode or a sandwich method AuNP/MgO/Pt—XC72/OxDc anode.

Figure 18A:
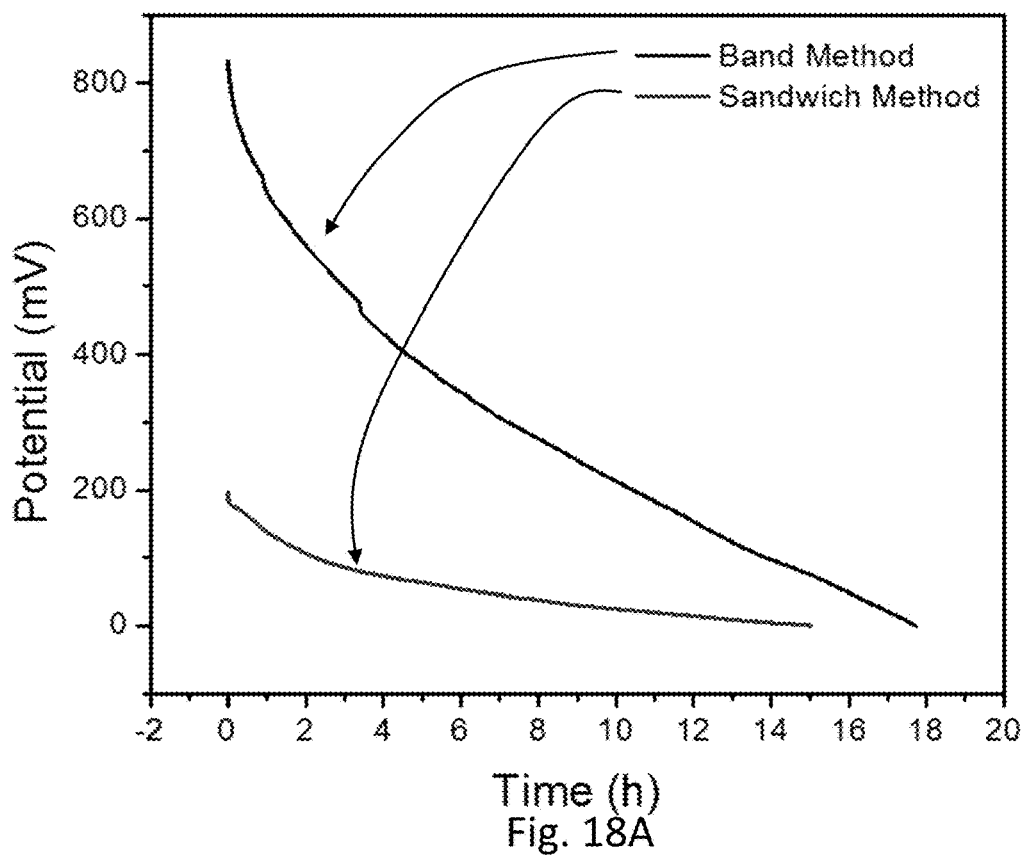
FIG. 18A shows data for representative discharge curves for glycerol fuel cells containing a BOx cathode and a band method AuNP/MgO/Pt—XC72/OxDc anode or a sandwich method AuNP/MgO/Pt—XC72/OxDc anode tested under a constant current load of 0.25 mA.
Figure 18B:
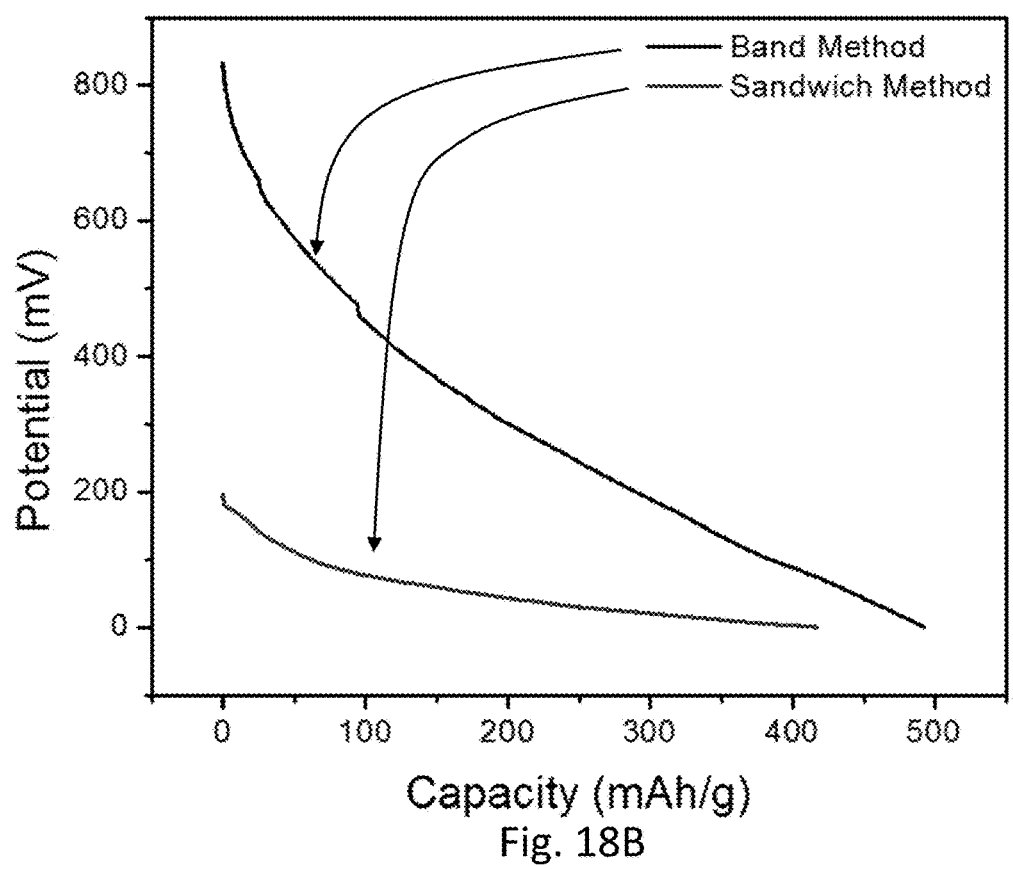
FIG. 18B shows data for representative capacity curves for glycerol fuel cells containing a BOx cathode and a band method AuNP/MgO/Pt—XC72/OxDc anode or a sandwich method AuNP/MgO/Pt—XC72/OxDc anode tested under a constant current load of 0.25 mA.

After generating power and current density curves, the fuel cells were placed under a constant current load of 0.25 mA (FIGS. 18A and 18B). Both fuel cells demonstrated good runtimes and capacities. Although the OCV was very low for the fuel cell containing the sandwich method hybrid anode, the specific capacity still reached over 400 mV. The specific capacity for the fuel cell containing the band method anode was 492 mAh/g. The specific capacity for the hybrid anode fuel cell was 36% higher than the metallic only anode fuel cell tested in the previous working period. The addition of the OxDc enzyme led to an increase in fuel cell runtime and capacity. The enhanced performance can be attributed to the breakdown of mesoxalic and oxalic acid to $CO_2$. FIG. 18A shows data for representative discharge curves for glycerol fuel cells containing a BOx cathode and a band method AuNP/MgO/Pt—XC72/OxDc anode or a sandwich method AuNP/MgO/Pt—XC72/OxDc anode tested under a constant current load of 0.25 mA. FIG. 18B shows data for representative capacity curves for glycerol fuel cells containing a BOx cathode and a band method AuNP/MgO/Pt—XC72/OxDc anode or a sandwich method AuNP/MgO/Pt—XC72/OxDc anode tested under a constant current load of 0.25 mA.

Figure 19A:
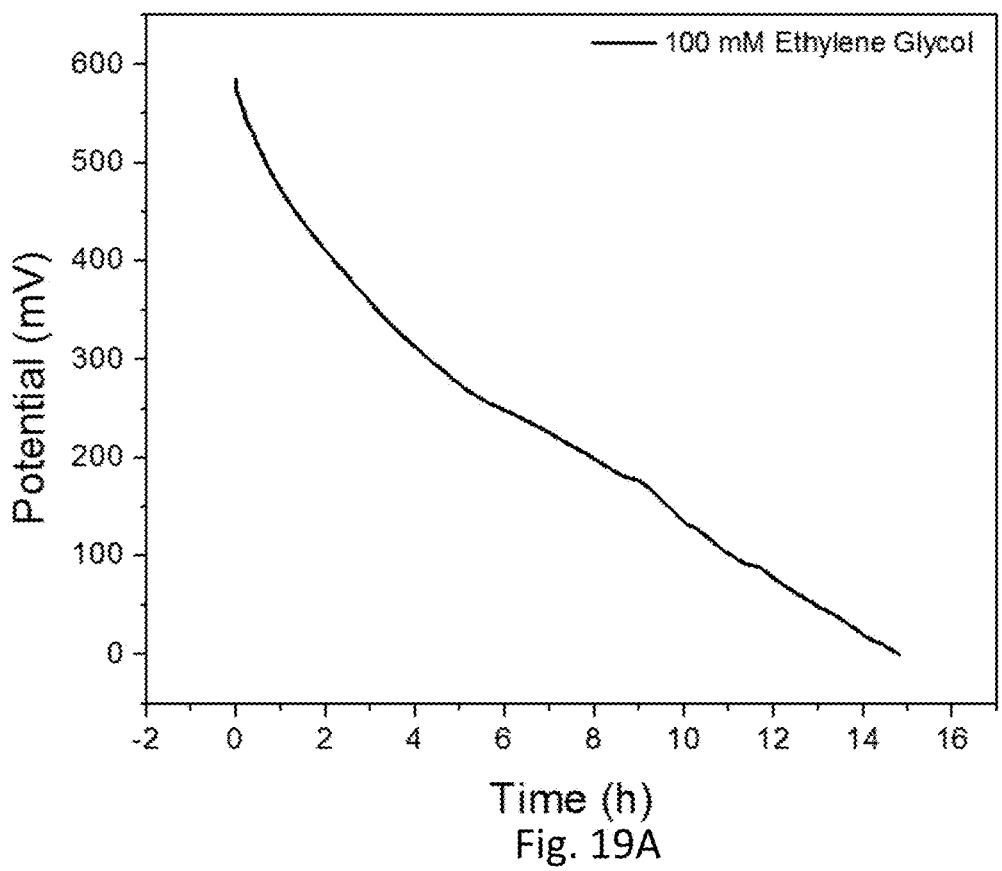
FIG. 19A shows data for representative discharge curves for ethylene glycol fuel cells containing a BOx cathode and a band method AuNP/MgO/Pt—XC72 anode tested under a constant current load of 0.25 mA.
Figure 19B:
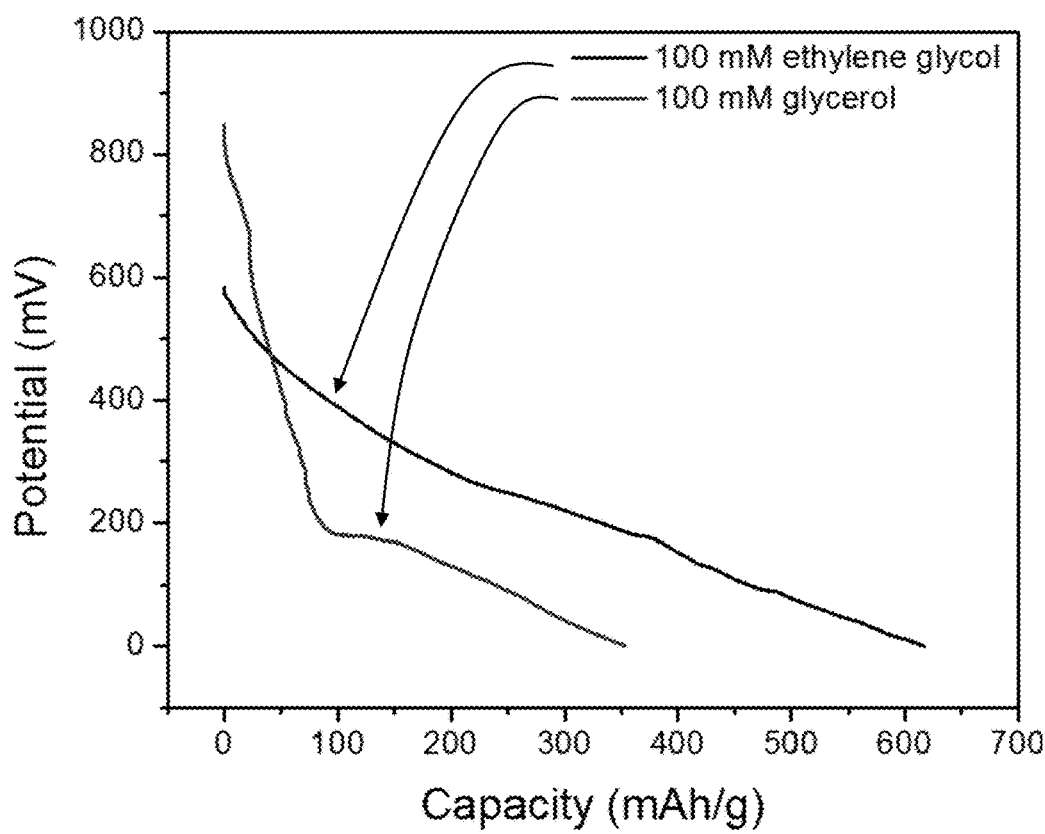
FIG. 19B shows data for representative capacity curves for ethylene glycol fuel cells or glycerol fuel cells containing a BOx cathode and a band method AuNP/MgO/Pt—XC72 anode tested under a constant current load of 0.25 mA.

Additionally, along with the hybrid anode testing, an ethylene glycol fuel cell test was conducted with the AuNP/MgO/Pt—XC72 anode (no OxDc) and a BOx cathode. The test was conducted to demonstrate the fuel flexibility capability of the new fuel cell system. The testing was conducted in the 7.3 cm$^2$ hardware with 100 mM ethylene glycol in PBS buffer as the primary fuel. The fuel cell ran for over 14 hours, and the specific capacity exceeded 600 mAh/g (FIGS. 19A and 19B). The capacity for the ethylene glycol fuel cell was 71% higher than the capacity for the glycerol fuel cell tested in the previous working period. Glycerol contains three hydroxyl groups whereas ethylene glycol contains only two, which makes ethylene glycol a simpler fuel to breakdown. The higher capacity of the ethylene glycol fuel cell could be attributed to more ethylene glycol being converted to oxalic acid. Theoretically, the complete oxidation of ethylene glycol and glycerol to $CO_2$ generates 10 and 14 electrons per molecule, respectively. However, ethylene glycol has several advantages over glycerol, which includes its lower molecular weight, fewer hydroxyl groups, fewer C—C bonds, and lower amount of intermediate reactions. The build-up of intermediate products could be the limiting factor for the glycerol fuel. FIG. 19A shows data for representative discharge curves for ethylene glycol fuel cells containing a BOx cathode and a band method AuNP/MgO/Pt—XC72 anode tested under a constant current load of 0.25 mA. FIG. 19B shows data for representative capacity curves for ethylene glycol fuel cells or glycerol fuel cells containing a BOx cathode and a band method AuNP/MgO/Pt—XC72 anode tested under a constant current load of 0.25 mA.

Table 3 summarizes the results for the hybrid anode fuel cells and the metallic anode fuel cells tested with 100 mM glycerol or 100 mM ethylene glycol fuel. Since ethylene glycol has a low molecular weight, the amount of substrate present in the ethylene glycol fuel cell (0.006 g) was approximately 33% lower than the amount of fuel present in the glycerol fuel cell (0.009 g) with the same concentration.

TABLE 3

Summary of complete fuel cell parameters and results:

| Anode Type | Substrate | Current Load (mA) | Amount of substrate (g) | Runtime (h) | Capacity mAh | mAh/g |
|---|---|---|---|---|---|---|
| AuNP/MgO/Pt-XC72 | 100 mM glycerol | 0.250 | 0.009 | 13.02 | 3.26 | 362 |
| AuNP/MgOPt-XC72/OxDc (band) | 100 mM glycerol | 0.250 | 0.009 | 17.72 | 4.43 | 492 |
| AuNP/MgO/Pt-XC72/OxDc (sandwich) | 100 mM glycerol | 0.250 | 0.009 | 15.03 | 3.76 | 417.5 |
| AuNP/MgO/Pt-XC72 | 100 mM ethylene glycol | 0.250 | 0.006 | 14.82 | 3.71 | 617.5 |

Figure 20:
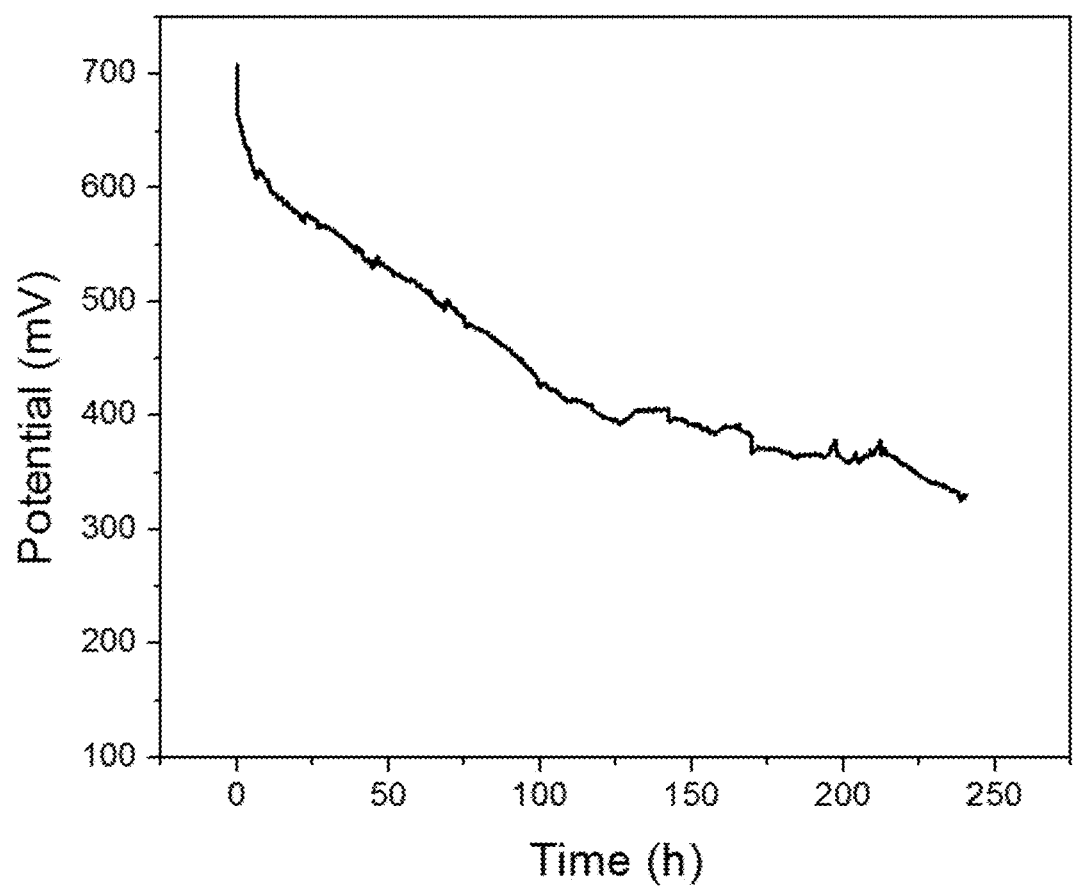
FIG. 20 includes data for a representative discharge curve for a flow-through (200 μl/min) glycerol fuel cell containing an AuNP/MgO/Pt—XC72 anode and a BOx cathode tested under a constant load of 0.25 mA.

In addition to batch mode fuel cell tests, a flow-through study was conducted with an AuNP/MgO/Pt—XC72 anode paired with a BOx cathode. The test was conducted in the 7.3 cm$^2$ hardware with 100 mM glycerol fuel. The fuel cell was placed under a constant current load of 0.25 mA. The potential of the fuel cell remained above 300 mV throughout testing (FIG. 20). A pH strip was used to measure the pH of the waste fuel. The pH of the glycerol flow-through cell waste was 8.0, which was slightly more basic than fresh glycerol fuel (pH 7.0). In comparison, the fuel waste from the flow-through mode fuel cell was less basic than the fuel waste from the batch mode fuel cells (pH 11.0). Since the catalytic activity of BOx decreases as the fuel pH increases, the lower activity of BOx could be a factor limiting the batch mode fuel cell performance. The extensive runtime of the flow-through cell was impressive, and demonstrated that both the metallic based anode and the BOx cathode can remain stable under optimal conditions. 240 hours of continuous fuel cell operation was demonstrated. The capacity of the fuel cell was 63 mAh. FIG. 20 includes data for a representative discharge curve for a flow-through (200 µl/min) glycerol fuel cell containing an AuNP/MgO/Pt—XC72 anode and a BOx cathode tested under a constant load of 0.25 mA.

Electrode Preparations:

7.3 cm$^2$ pieces of carbon felt (0.125 inch thick) were cut out, and sliced in two (lengthwise). The carbon felt electrodes were plasma cleaned on high for 5 minutes. Afterwards, the electrodes were rinsed with IPA and water (excess liquid removed with paper towel). A three-electrode cell with 15 ml of 2 M KOH was set-up. A potential load of 1.2 V was applied to the carbon felt electrodes for 10 min. Then the electrodes were rinsed with water (excess liquid removed with paper towel). The electrodes were stored at room temperature for at least 2 hours before ink deposition. The AuNP/MgO/Pt—XC72 ink was prepared by mixing Plat-XC72 (45.6 mg) and MgO (91.25 mg) with AuNPs (1.825 ml). After sonicating the solution for 30 seconds, 12.2 µl of PTFE was added to the AuNP solution. After mixing (e.g., vortexing) the solution, the metallic ink was drop casted onto the carbon felt electrodes following the band method. The OxDc ink was prepared by adding 50 µl of OxDc to 750 µl of EGDE/CFDRC Ink. The OxDc ink solution was mixed (e.g., vortexed), and then drop casted onto the carbon felt electrodes following the band method. The band method involved drop casting AuNP/MgO/Pt—XC72 onto half of each piece of carbon felt, and OxDc onto the other half of each piece of carbon felt. When the fuel cell was assembled, the AuNP/MgO/Pt—XC72 side of CF-1.1 was in contact with the AuNP/MgO/Pt—XC72 side of CF-2.1. The band method allowed for the incorporation of OxDc into the metallic catalyst based anode without mixing the OxDc directly into the metallic ink. FIG. 16A could also represent a schematic representation of the band method employed for drop casting AuNP/MgO/Pt—XC72 solution and OxDc ink onto carbon felt electrodes.

Figure 21:
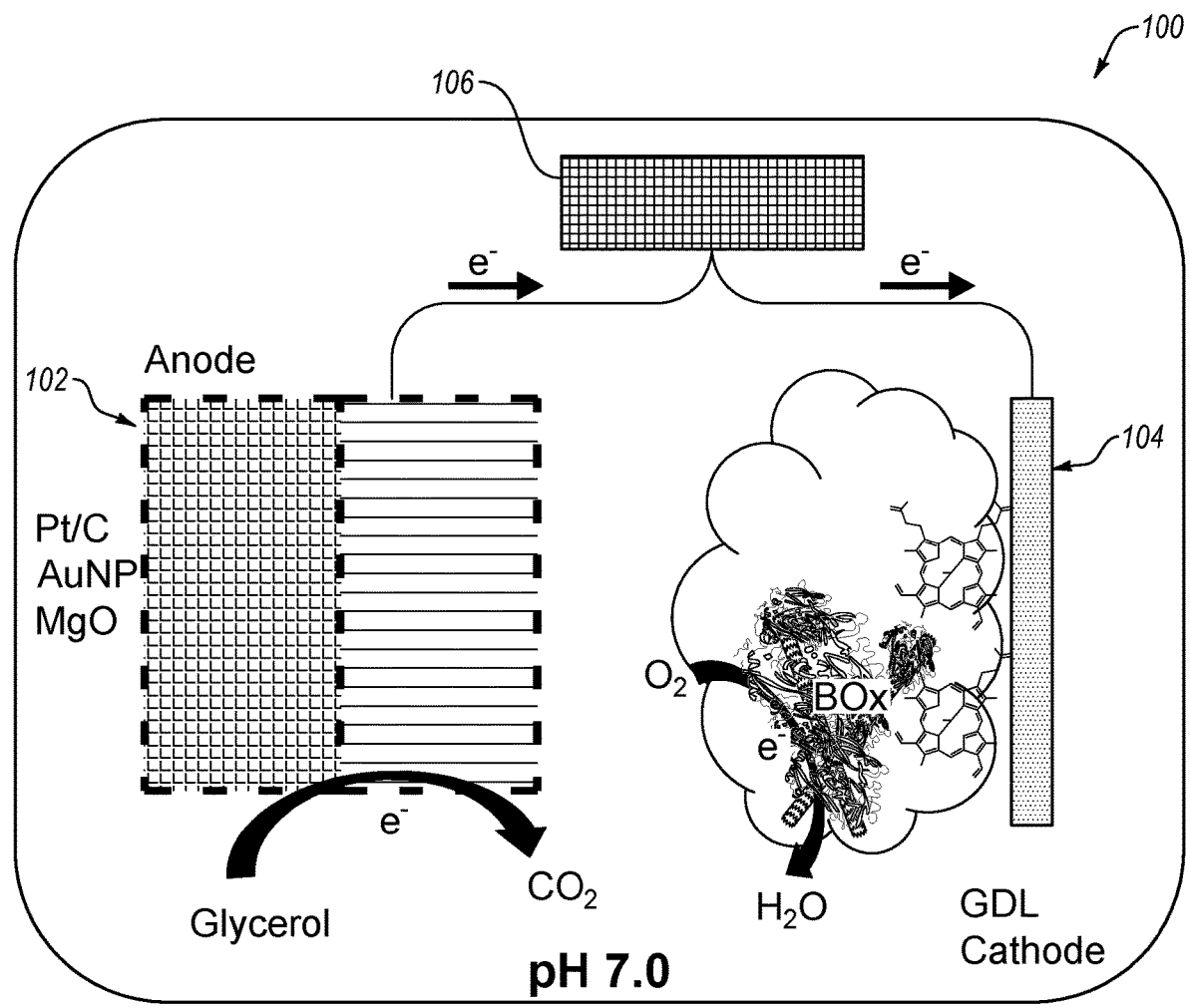
FIG. 21 shows a schematic illustration of a biofuel cell having a hybrid AuNP/MgO bioanode combined with a hematin modified BOx biocathode for oxidation of glycerol in a mediatorless-membraneless biofuel cell under optimized neutral pH conditions (PBS buffer, pH7.0).

FIG. 21 shows a schematic illustration of a biofuel cell 100 having a hybrid AuNP/MgO bioanode 102 combined with a hematin modified BOx biocathode 104 for oxidation of glycerol in a mediatorless-membraneless biofuel cell under optimized neutral pH conditions (PBS buffer, pH7.0).

A potentiostat 106 is electrically connected to the bioanode 102 and also electrically connected to the biocathode 104 such that electrons pass from the bioanode 102, through the potentiostat 106 and to the biocathode 104 upon glycerol being converted by the bioanode 104 to produce $CO_2$ and $O_2$ being converted to $H_2O$ by the biocathode 104 at about neutral pH (pH 7.0). The reactions are shown in FIG. 21.

With respect to the use of substantially any plural and/or singular terms herein, those having skill in the art can translate from the plural to the singular and/or from the singular to the plural as is appropriate to the context and/or application. The various singular/plural permutations may be expressly set forth herein for sake of clarity.

It will be understood by those within the art that, in general, terms used herein, and especially in the appended claims (e.g., bodies of the appended claims) are generally intended as "open" terms (e.g., the term "including" should be interpreted as "including but not limited to," the term "having" should be interpreted as "having at least," the term "includes" should be interpreted as "includes but is not limited to," etc.). It will be further understood by those within the art that if a specific number of an introduced claim recitation is intended, such an intent will be explicitly recited in the claim, and in the absence of such recitation, no such intent is present. For example, as an aid to understanding, the following appended claims may contain usage of the introductory phrases "at least one" and "one or more" to introduce claim recitations. However, the use of such phrases should not be construed to imply that the introduction of a claim recitation by the indefinite articles "a" or "an" limits any particular claim containing such introduced claim recitation to embodiments containing only one such recitation, even when the same claim includes the introductory phrases "one or more" or "at least one" and indefinite articles such as "a" or "an" (e.g., "a" and/or "an" should be interpreted to mean "at least one" or "one or more"); the same holds true for the use of definite articles used to introduce claim recitations. In addition, even if a specific number of an introduced claim recitation is explicitly recited, those skilled in the art will recognize that such recitation should be interpreted to mean at least the recited number (e.g., the bare recitation of "two recitations," without other modifiers, means at least two recitations, or two or more recitations). Furthermore, in those instances where a convention analogous to "at least one of A, B, and C, etc." is used, in general, such a construction is intended in the sense one having skill in the art would understand the convention (e.g., "a system having at least one of A, B, and C" would include but not be limited to systems that have A alone, B alone, C alone, A and B together, A and C together, B and C together, and/or A, B, and C together, etc.). In those instances where a convention analogous to "at least one of A, B, or C, etc." is used, in general, such a construction is intended in the sense one having skill in the art would understand the convention (e.g., "a system having at least one of A, B, or C" would include but not be limited to systems that have A alone, B alone, C alone, A and B together, A and C together, B and C together, and/or A, B, and C together, etc.). It will be further understood by those within the art that virtually any disjunctive word and/or phrase presenting two or more alternative terms, whether in the description, claims, or drawings, should be understood to contemplate the possibilities of including one of the terms, either of the terms, or both terms. For example, the phrase "A or B" will be understood to include the possibilities of "A" or "B" or "A and B."

In addition, where features or aspects of the disclosure are described in terms of Markush groups, those skilled in the art will recognize that the disclosure is also thereby described in terms of any individual member or subgroup of members of the Markush group.

As will be understood by one skilled in the art, for any and all purposes, such as in terms of providing a written description, all ranges disclosed herein also encompass any and all possible subranges and combinations of subranges thereof. Any listed range can be easily recognized as sufficiently describing and enabling the same range being broken down into at least equal halves, thirds, quarters, fifths, tenths, etc. As a non-limiting example, each range discussed herein can be readily broken down into a lower third, middle third and upper third, etc. As will also be understood by one skilled in the art all language such as "up to," "at least," and the like include the number recited and refer to ranges which can be subsequently broken down into subranges as discussed above. Finally, as will be understood by one skilled in the art, a range includes each individual member. Thus, for example, a group having 1-3 cells refers to groups having 1, 2, or 3 cells. Similarly, a group having 1-5 cells refers to groups having 1, 2, 3, 4, or 5 cells, and so forth.

From the foregoing, it will be appreciated that various embodiments of the present disclosure have been described herein for purposes of illustration, and that various modifications may be made without departing from the scope and spirit of the present disclosure. Accordingly, the various embodiments disclosed herein are not intended to be limiting, with the true scope and spirit being indicated by the following claims.

This patent application cross-references U.S. Pat. Nos. 8,685,286 and 8,703,022, which are incorporated herein by specific reference in their entirety.

All references recited herein are incorporated herein by specific reference in their entirety.

REFERENCES

1) L. Xin, Z. Zhang, Z. Wang and L. Wenzhen, "Simultaneous Generation of Mesoxalic Acid and Electricity from Glycerol on a Gold Anode Catalyst in Anion-Exchange Membrane Fuel Cells," *Chem Cat Chem*, vol. 4, pp. 1105-1114, 2012.
2) G. L. Brett, Q. He, C. M. P. J. Hammond, N. Dimitratos, M. Sankar, A. A. Herzing, M. Conte, J. A. Lopez-Sanchez, C. J. Kiely, D. W. Knight, S. H. Taylor and G. and Hutchings, "Selective Oxidation of Glycerol by Highly Active Bimetallic Catalysts at Ambient Temperature under Base-Free Conditions," *Communications*, vol. 50, pp. 10136-10139, 2011.
3) A. Villa, S. Campisi, K. M. H. Mohammed, N. Dimitratos, F. Vindigni, M. Manzoli, W. Jones, M. Bowker, G. J. Hutchings and L. Prati, "Tailoring the selectivity of glycerol oxidation by tuning the acid-base properties of Au catalyst," *Catalysis Science and Technology*, vol. 5, pp. 1126-1132, 2015.
4) E. Pinchon, M. Arugula, K. Pant, and S. Singhal, "Enhancement of Electrochemical Performance of Bilirubin Oxidase Modified Gas Diffusion Biocathode by Porphyrin Precursor," Advances in Physical Chemistry, vol. 2018, 9 pages, 2018. doi.org/10.1155/2018/4712547.
5) M. Arugula, E. Pinchon, K. Pant, S. D. Minteer, S. Singhal, "Enhancement of Electrochemical performance of Bilirubin Oxidase Modified Gas Diffusion Biocathode By Porphyrin Precursor," In: Proceedings from the Electrochemical Society Meetings; May 13-17, 2018; Seattle, Wash. Abstract MA2018-01 2245.

6) M. Arugula, E. Pinchon, U. Lindstrom, P. Juzang, K. Pant, S. D. Minteer, S. Singhal, "Hybrid Non-Enzymatic and Enzymatic Cascade Bioanode for Glycerol/02 Biofuel Cell Applications," In: Proceedings from the Electrochemical Society Meetings; May 13-17, 2018; Seattle, Wash. Abstract MA2018-01 2251.

The invention claimed is:

1. A cathode comprising:
    an electrode substrate;
    a porphyrin precursor attached to the substrate, wherein the porphyrin precursor is hematin; and
    a mixture including an enzyme, wherein the mixture is linked through the porphyrin precursor to the substrate such that the porphyrin precursor is between the substrate and the mixture, wherein the enzyme reduces oxygen.

2. The cathode of claim 1, wherein the mixture comprises a conductive material linked to the enzyme.

3. The cathode of claim 2, wherein the mixture comprises 1-pyrenebutanoic acid, succinimidyl ester (PBSE) linked to the conductive material.

4. The cathode of claim 3, wherein the mixture comprises 2,5-dimethyl-1-phenyl-1H-pyrrole-3-carbaldehyde (DMY-Carb) linked with the 1-pyrenebutanoic acid, succinimidyl ester (PBSE) and the DMY-Carb is linked to the enzyme.

5. The cathode of claim 4, wherein the porphyrin precursor links the mixture having the enzyme to the electrode substrate and the conductive material is linked to the enzyme by the PBSE being linked to the conductive material and the PBSE linking with the DMY-carb that is attached to the enzyme.

6. The cathode of claim 2, wherein:
    the enzyme is bilirubin oxidase (BOx); and
    the conductive material is multi-wall carbon nanotubes (MWCNT).

7. The cathode of claim 6, further comprising a binder associated with the porphyrin precursor, enzyme, and conductive material.

8. The cathode of claim 6, comprising KOH or NaOH as an alkaline substance associated with the porphyrin precursor.

9. The cathode of claim 7, further comprising a binder being selected from the group consisting of tetramethyl orthosilicate (TMOS), tetraethyl orthosilicate (TEOS), and combinations thereof.

10. The cathode of claim 1, wherein the electrode substrate is selected from a group consisting of carbon felt, buckypaper, pressed teflonized carbon black powder, pressed teflonized carbon black powder having carbon nanotubes, buckeye composite, carbon felt, buckeye paper, toray paper, glassy carbon, carbon cloth, carbon paper (toray), carbon paper (ELAT), carbon screen printed electrodes, and combinations thereof.

11. The cathode of claim 1, comprising an alkaline substance associated with the porphyrin precursor.

12. The cathode of claim 11, comprising a hydroxide as the alkaline substance.

13. The cathode of claim 1, wherein the porphyrin precursor is attached to the substrate through covalent coupling with 1-ethyl-3-(3-dimethylaminopropyl)carbodiimide hydrochloride (EDC), and N-hydroxysuccinimide (NHS).

14. A cathode region of a biofuel cell, comprising:
    the cathode of claim 1; and
    a neutral fuel liquid in contact with the cathode, the neutral fuel liquid having a neutral pH.

15. The cathode region of claim 14, wherein the neutral fuel liquid includes an alcohol, polyol, carbohydrate, or combination thereof.

16. A fuel cell comprising:
    the cathode of claim 1;
    an anode; and
    a neutral fuel liquid in contact with the anode and cathode, the neutral fuel liquid having a neutral pH and the fuel reagent.

17. The fuel cell of claim 16, wherein the anode includes an anode enzyme.

18. A manufacturing method of making the cathode of claim 1, the method comprising:
    forming the electrode substrate;
    attaching the porphyrin precursor to the electrode substrate; and
    linking the mixture having the enzyme to the porphyrin precursor.

19. The manufacturing method of claim 18, comprising forming the electrode substrate by:
    combining teflonized carbon black powder and carbon nanotubes; and
    pressing the teflonized carbon black powder and carbon nanotubes into the electrode substrate.

20. The manufacturing method of claim 18, comprising:
    treating the electrode substrate with EDC and NHS;
    combining the porphyrin precursor with a hydroxide; and
    depositing the porphyrin precursor and hydroxide on the treated electrode substrate.

21. The manufacturing method of claim 18, comprising:
    preparing a BOx ink as follows:
        forming an alcoholic aqueous solution;
        adding carbon nanotubes to the alcoholic aqueous solution;
        adding 2,5-dimethyl-1-phenyl-1H-pyrrole-3-carbaldehyde (DMY-Carb) to a solvent;
        combining the DMY-carb in solvent with the alcoholic aqueous solution having the carbon nanotubes; and
        adding 1-pyrenebutanoic acid, succinimidyl ester (PBSE) to the composition having the DMY-carb and carbon nanotubes; and
    depositing a BOx ink on the electrode substrate having the porphyrin precursor.

22. A fuel cell comprising:
    a cathode comprising:
        an electrode substrate;
        a porphyrin precursor attached to the substrate; and
        an enzyme, wherein the enzyme is one of coupled to the electrode substrate so as to be associated with the porphyrin precursor or a mixture including the enzyme is linked through the porphyrin precursor to the substrate, wherein the enzyme reduces oxygen;
    an anode comprising:
        an anode electrode substrate;
        a first region of the anode substrate having a gold nanoparticle composition located thereon; and
        a second region of the anode substrate having an enzyme composition located thereon,
        wherein the first region and second region are separate regions; and
    a neutral fuel liquid in contact with the anode and cathode, the neutral fuel liquid having a neutral pH and the fuel reagent.

23. The fuel cell of claim 22, comprising one or more of the following:
    the gold nanoparticle composition includes a conductive material mixed with the gold nanoparticles;

the gold nanoparticle composition includes a binder mixed with the gold nanoparticles;

the anode electrode substrate is selected from the group consisting of carbon felt, buckypaper, carbon cloth, carbon paper (toray), carbon paper (ELAT), carbon screen printed electrodes, and combinations thereof;

the anode substrate has a surface and the gold nanoparticle composition is deposed on a first portion of the surface and the enzyme composition is deposed on a second portion of the surface;

the enzyme composition includes an enzyme selected from the group consisting of oxalate decarboxylase (OxDc), oxalate oxidase (OxO), aldehyde dehydrogenase (ALDH), alcohol dehydrogenase (ADH), formate dehydrogenase, formaldehyde dehydrogenase, glucose dehydrogenase, lactic dehydrogenase and pyruvate dehydrogenase, and combinations thereof; or about half of a surface of the anode substrate includes the gold nanoparticle composition and about half of the surface of the anode substrate includes the enzyme composition.

24. The fuel cell of claim 22, the anode comprising:

a first anode substrate having a first gold nanoparticle composition region and a first enzyme composition region; and a second anode substrate having a second gold nanoparticle composition region and a second enzyme composition region, wherein the first anode substrate contacts the second anode substrate such that the first gold nanoparticle composition contacts the second gold nanoparticle composition and the first enzyme composition contacts the second enzyme composition.

25. The fuel cell of claim 22, the anode comprising:

an anode substrate having a hydroxide composition thereon;

a first region of the anode substrate having a gold nanoparticle composition located thereon on the hydroxide composition; and a second region of the anode substrate having an enzyme composition located thereon on the hydroxide composition, wherein the combination of the gold nanoparticle composition and enzyme composition converts a fuel reagent to carbon dioxide at neutral pH, wherein the first region and second region are separate regions.

* * * * *